(12) United States Patent
Reddy et al.

(10) Patent No.: US 9,012,491 B2
(45) Date of Patent: Apr. 21, 2015

(54) HETEROCYCLIC BORONIC ACID ESTER DERIVATIVES AND THERAPEUTIC USES THEREOF

(75) Inventors: Raja K. Reddy, San Diego, CA (US); Serge Henri Boyer, San Diego, CA (US); Maxim Totrov, San Diego, CA (US); Scott Hecker, Del Mar, CA (US)

(73) Assignee: Rempex Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 14/241,412

(22) PCT Filed: Aug. 30, 2012

(86) PCT No.: PCT/US2012/053233
§ 371 (c)(1),
(2), (4) Date: Feb. 26, 2014

(87) PCT Pub. No.: WO2013/033461
PCT Pub. Date: Mar. 7, 2013

(65) Prior Publication Data
US 2014/0206648 A1 Jul. 24, 2014

Related U.S. Application Data

(60) Provisional application No. 61/529,859, filed on Aug. 31, 2011.

(51) Int. Cl.
| | | |
|---|---|---|
| A61K 31/381 | (2006.01) | |
| C07D 333/10 | (2006.01) | |
| A61K 31/69 | (2006.01) | |
| A61K 45/06 | (2006.01) | |
| A61K 31/427 | (2006.01) | |
| A61K 31/43 | (2006.01) | |
| A61K 31/546 | (2006.01) | |
| C07F 5/02 | (2006.01) | |
| A61K 31/426 | (2006.01) | |
| A61K 47/26 | (2006.01) | |
| A61K 9/08 | (2006.01) | |
| A61K 9/00 | (2006.01) | |

(52) U.S. Cl.
CPC ............... *A61K 31/69* (2013.01); *A61K 45/06* (2013.01); *A61K 31/427* (2013.01); *A61K 31/43* (2013.01); *A61K 31/546* (2013.01); *C07F 5/025* (2013.01); *A61K 31/426* (2013.01); *A61K 9/0014* (2013.01); *A61K 9/0019* (2013.01); *A61K 47/26* (2013.01); *A61K 9/08* (2013.01)

(58) Field of Classification Search
CPC ............................ A61K 31/381; C07D 333/10
USPC ................................. 549/29, 74, 76; 514/438
See application file for complete search history.

(56) References Cited

U.S. PATENT DOCUMENTS

| | | | |
|---|---|---|---|
| 4,194,047 A | 3/1980 | Christensen et al. | |
| 4,260,543 A | 4/1981 | Miller | |
| 4,409,214 A | 10/1983 | Takaya et al. | |
| 4,822,786 A | 4/1989 | Zama et al. | |
| 5,888,998 A | 3/1999 | Maiti et al. | |
| 6,184,363 B1 | 2/2001 | Shoichet et al. | |
| 6,586,615 B1 | 7/2003 | Kettner et al. | |
| 7,271,186 B1 | 9/2007 | Shoichet et al. | |
| 7,439,253 B2 | 10/2008 | Lampilas et al. | |
| 7,582,621 B2 | 9/2009 | Baker et al. | |
| 7,612,087 B2 | 11/2009 | Aszodi et al. | |
| 8,680,136 B2 * | 3/2014 | Hirst et al. | ..................... 514/438 |
| 2004/0019203 A1 | 1/2004 | Micetich et al. | |
| 2004/0157826 A1 | 8/2004 | Lampilas et al. | |
| 2005/0020572 A1 | 1/2005 | Aszodi et al. | |
| 2006/0019116 A1 | 1/2006 | Conley et al. | |
| 2006/0178357 A1 | 8/2006 | Buynak et al. | |
| 2006/0210883 A1 | 9/2006 | Chen et al. | |
| 2010/0056478 A1 | 3/2010 | Desarbre et al. | |
| 2010/0120715 A1 | 5/2010 | Burns et al. | |
| 2010/0256092 A1 | 10/2010 | Xia et al. | |
| 2011/0288063 A1 | 11/2011 | Maiti et al. | |
| 2012/0040932 A1 | 2/2012 | Hirst et al. | |
| 2013/0316978 A1 | 11/2013 | Reddy et al. | |
| 2013/0331355 A1 | 12/2013 | Griffith et al. | |
| 2013/0345172 A1 | 12/2013 | Hirst et al. | |
| 2014/0194284 A1 | 7/2014 | Reddy et al. | |
| 2014/0194381 A1 | 7/2014 | Reddy et al. | |
| 2014/0194382 A1 | 7/2014 | Reddy et al. | |
| 2014/0194385 A1 | 7/2014 | Reddy et al. | |

(Continued)

FOREIGN PATENT DOCUMENTS

| | | |
|---|---|---|
| EP | 1550657 A1 | 7/2005 |
| JP | 2003-229277 | 8/2003 |
| JP | 2004-291253 | 10/2004 |

(Continued)

OTHER PUBLICATIONS

Abdel-Magid et al., "Reductive Amination of Aldehydes and Ketones with Sodium Triacetoxyborohydride: Studies on Direct and Indirect Reductive Amination Procedures", J Org Chem. (1996) 61(11):3849-3862.

Adediran et al., "A 'cephalosporin-like' cyclic depsipeptide: Synthesis and reaction with beta-lactam-recognizing enzymes", Bioorg Med Chem Lett. (1999) 9(3):341-346.

Aizpurua et al., "Synthesis of benzyl halides from aldehydes promoted by halosilanes and 1,1,3,3-tetramethyldisiloxane (TMDS)", Tetrahedron Lett. (1984) 25(10):1103-1104.

Akiyama et al., "*N*-Hydroxy Amides. Part 6. Synthesis and Spectroscopic Properties of 1-Hydroxypiperazine-2,5-diones", J Chem Soc., Perkin Trans I, (1989) 2:235-239.

Allen et al., "Ansel's Pharmaceutical Dosage Forms and Drug Delivery Systems", 8th Edition (2004) TOC only.

Arya et al., "Advances in asymmetric enolate methodology", Tetrahedron (2000) 56:917-947.

(Continued)

*Primary Examiner* — Golam M M Shameem

(74) *Attorney, Agent, or Firm* — Knobbe, Martens, Olson & Bear, LLP

(57) ABSTRACT

Disclosed herein are antimicrobial compounds compositions, pharmaceutical compositions, the use and preparation thereof. Some embodiments relate to cyclic boronate compounds and their use as therapeutic agents.

39 Claims, No Drawings

(56) References Cited

U.S. PATENT DOCUMENTS

| | | |
|---|---|---|
| 2014/0194386 A1 | 7/2014 | Burns et al. |
| 2014/0206648 A1 | 7/2014 | Reddy et al. |

FOREIGN PATENT DOCUMENTS

| | | |
|---|---|---|
| WO | WO 87/05297 | 9/1987 |
| WO | WO 89/10961 | 11/1989 |
| WO | WO 98/56392 A1 | 12/1998 |
| WO | WO 00/35904 A1 | 6/2000 |
| WO | WO 00/35905 A1 | 6/2000 |
| WO | WO 01/23374 A1 | 4/2001 |
| WO | WO 01/30149 | 5/2001 |
| WO | WO 02/22137 A1 | 3/2002 |
| WO | WO 02/83884 | 10/2002 |
| WO | WO 03/070714 | 8/2003 |
| WO | WO 2004/039859 | 5/2004 |
| WO | WO 2004/058679 A2 | 7/2004 |
| WO | WO 2004/064755 A2 | 8/2004 |
| WO | WO 2005/033090 | 4/2005 |
| WO | WO 2005/035532 A1 | 4/2005 |
| WO | WO 2005/087700 | 9/2005 |
| WO | WO 2006/091771 | 8/2006 |
| WO | WO 2007/058602 A2 | 5/2007 |
| WO | WO 2007/065288 A2 | 6/2007 |
| WO | WO 2007/095638 | 8/2007 |
| WO | WO 2008/039420 A2 | 4/2008 |
| WO | WO 2008/116813 A1 | 10/2008 |
| WO | WO 2009/046098 A1 | 4/2009 |
| WO | WO 2009/064413 A1 | 5/2009 |
| WO | WO 2009/064414 A1 | 5/2009 |
| WO | WO 2009/091856 A1 | 7/2009 |
| WO | WO 2009/117540 A1 | 9/2009 |
| WO | WO 2009/139834 A1 | 11/2009 |
| WO | WO 2009/140309 A2 | 11/2009 |
| WO | WO 2010/056827 A1 | 5/2010 |
| WO | WO 2010/075286 A1 | 7/2010 |
| WO | WO 2010/097675 A1 | 9/2010 |
| WO | WO 2010/130708 A1 | 11/2010 |
| WO | WO 2010/144338 A1 | 12/2010 |
| WO | WO 2011/017125 A1 | 2/2011 |
| WO | WO 2011/103686 A1 | 9/2011 |
| WO | WO 2012/021455 A1 | 2/2012 |
| WO | WO 2012/067664 A1 | 5/2012 |
| WO | WO 2012/106995 A1 | 8/2012 |
| WO | WO 2013/033461 A1 | 3/2013 |
| WO | WO 2013/053372 A1 | 4/2013 |
| WO | WO 2013/056163 A1 | 4/2013 |
| WO | WO 2013/092979 A1 | 6/2013 |
| WO | WO 2013/122888 A2 | 8/2013 |
| WO | WO 2014/089365 A1 | 6/2014 |
| WO | WO 2014/151958 A1 | 9/2014 |

OTHER PUBLICATIONS

Babic et al., "What's new in antibiotic resistance? Focus on beta-lactamases", Drug Res Updates (2006) 9:142-156.
Bassetti et al., "New antibiotics for bad bugs: where are we?", Ann Clin Microbiol Antimicrob. (2013) 12:22-36.
Becker, Daniel E., "Antimicrobial Drugs", Anesth Prog (2013) 60:111-123.
Beenen et al., "Asymmetric copper-catalyzed synthesis of alpha-amino boronate esters from N-tert-butanesulfinyl aldimines", J Am Chem Soc. (2008) 130(22):6910-6911.
Biedrzycki et al., "Derivatives of tetrahedral boronic acids", J. Organomet. Chem. (1992) 431:255-270.
Bou et al., "Cloning, nucleotide sequencing, and analysis of the gene encoding an AmpC beta-lactamase in *Acinetobacter baumannii*", Antimicrob Agents Chemother (2000) 44(2):428-432.
Bou et al., "OXA-24, a novel class D beta-lactamase with carbapenemase activity in an *Acinetobacter baumannii* clinical strain", Antimicrob Agents Chemother (2000) 44(6):1556-1561 and Erratum: Antimicrob Agents Chemother (2006) 50(6) 2280.
Brabez et al., "Design,synthesis, and biological studies of efficient multivalent melanotropin ligands: tools toward melanoma diagnosis and treament", J Med Chem. (2011) 54(20):7375-7384.

Brosz et al., "Resolution of alpha-aminoboronic esters by diastereoselective crystallization with pinanediols. Confirmation by x-ray analysis", Tetrahedron: Asymmetry (1997) 8(9):1435-1440.
Bush et al., "Minireview: Updated Functional Classification of beta-Lactamases," Antimicrob Agents Chemo. (2010) 54(3):969-976.
Cheng et al., "Synthesis of Aryl Thioethers through the N-Chlorosuccinimide-Promoted Cross-Coupling Reaction of Thiols with Grignard Reagents", J Org Chem. (2012) 77(22):10369-10374.
Clinical and Laboratory Standards Institute (formerly NCCLS, National Committee for Clinical Laboratory Standards). "Methods for Dilution of Antimicrobial Susceptibility Tests for Bacteria That Grow Aerobically", CLSI (Jan. 2006) M7-A7 26(2), 64 pages.
Clinical and Laboratory Standards Institute (formerly NCCLS, National Committee for Clinical Laboratory Standards). "Methods for Dilution of Antimicrobial Susceptibility Tests for Bacteria That Grow Aerobically", CLSI (Jan. 2009) M07-A8 29(2), 88 pages.
Coppa et al., "A Facile, Convenient and Selective Homolytic Carbamolylation of Heteroaromatic Bases", Heterocycles (1993) 36(12):2687-2696.
Coutts et al., "Two Efficient Methods for the Cleavage of Pinanediol Boronate Esters Yielding the Free Boronic Acids", Tetrahedron Ltt. (1994) 35(29):5109-5112.
Darses et al., "Potassium Organotrifluoroborates: New Perspectives in organic Synthesis", Chem Rev. (2008) 108:288-325.
Davoli et al., "Enantioselective total synthesis of (-)-microcarpalide", Tetrahedron (2005) 61:4427-4436.
Di Gioia et al., "Optically Pure *N*-Hydroxy-O-triisopropylsilyl-alpha-L-amino Acid Methyl Esters from AICI3-Assisted Ring Opening of Chiral Oxaziridines by Nitrogen Containing Nucleophiles", J Org Chem. (2005) 70(25):10494-10501.
Endo et al., "Chemoselective Suzuki coupling of diborylmethane for facile synthesis of benzylboronates", Org Lett. (2011) 13(13):3368-3371.
Eidam et al., "Design, synthesis, crystal structures and antimicrobial activity of sulfonamide boronic acids as beta-lactamase inhibitors", J Med Chem. (2010) 53(21):7852-7863.
Eissenstat et al., "Aminoalkylindoles: Structure-Activity Relationships of Novel Cannabinoid Mimetics", J Med Chem. (1995) 38(16):3094-3105.
El Nezhawy et al., "Synthesis and antioxidant activity of some thiazolidin-4-one derivatives", Springer; Chemical Monthly/Monatshefte für Chemie (2009) 140(5):531-539.
Fan, et al. (2009): STN International HCAPLUS database, Columbus (OH), accession No. 2009: 425839; 6 pages.
Farquhar et al., "Intensely potent doxorubicin analogues: structure—activity relationship", J. Med. Chem. (1998) 41(6):965-972.
Ghosh et al., "Enantioselective total synthesis of (+)-largazole, a potent inhibitor of histone deacetylase", Org Lett. (2008) 10(17):3907-3909.
Giroux, A., "Synthesis of benzylic boronates via palladium-catalyzed cross-coupling reaction of bis(pinacolato)diboron with benzylic halides", Tetrahedron Lett. (2003) 44:233-235.
Gossinger et al., "Towards EPC-syntheses of the structural class of cochleamycins and macquarimicins. Part 3: EPC-syntheses of the beta-keto lactone subunits and first attempts towards the syntheses of the pentacyclic antibiotics of this group", Tetrahedron (2007) 63:8336-8350.
Hama et al., "Palladium-Catalyzed alpha-Arylation of Zinc Enolates of Esters: Reaction Conditions and Substrate Scope", J Org Chem. (2013) 78(17):8250-8266.
Imanishi et al., "Discovery of a Novel Series of Biphenyl Benzoic Acid Derivatives as Potent and Selective Human beta3-Adrenergic Receptor Agonists with Good Oral Bioavailability. Part I", J Med Chem. (2008) 51(6):1925-1944.
Inglis et al., "Observations on the Deprotection of Pinanediol andPpinacol Boronate Esters via Fluorinated Intermediates", J Org Chem. (2010) 75(2):468-471.
Ishii et al, "In vitro potentiation of carbapenems with ME1071, a Novel metallo-β-lactamase inhibitor, against metallo-β-lactamase producing *Pseudomonas aeruginosa* clinical isolates." Antimicrob. Agents Chemother. doi:10.1128/AAC.01397-09 (2010) 54(9):3625-3629.

(56) References Cited

OTHER PUBLICATIONS

Ito et al., "An efficient constructive method for a tricyclic system: an important intermediate for the synthesis of tricycloclavulone", Tetrahedron Lett. (2003) 44:1259-1261.
Jadhav et al., "Direct synthesis of [alpha-[(tert-Butoxycarbonyl)amino]alkyl]- boronates from (alpha-Haloalkyl)boronates", Org Chem. (1996) 61(22):7951-7954.
Jagannathan et al., "Synthesis of Boronic Acid Analogues of alpha-Amino Acids by Introducing Side Chains as Electrophiles", J Org Chem. (2001) 66(19):6375-6380.
Jiang et al., "A Practical Synthesis of Cefcapene Pivoxil", Synthesis (2012) 44:207-214.
Kanai et al., "Synthesis of ortho-Acylbenzylboronates via Cross-Coupling Reaction of (Dialkoxyboryl)methylzinc Reagents with Haloarenes. A Stable ortho-Quinodimethane Precursor", (1993) 22(5):845-848.
Kint et al., "New-found fundamentals of bacterial persistance", Trends Microbiol. (2012) 20(12):577-585.
Kose et al., "Synthesis of photochromic 2,3-bis(5-methyl-2-phenyl-4-thiazolyl)-1,4-naphthoquinone derivatives", J Photochem Photobiol. A: Chemistry. (2011) 219(1):58-61.
Kotha et al., "Recent applications of the suzuki-miyaura cross-coupling reaction in organic synthesis", Tetrahedron (2002) 58:9633-9695.
Kumar et al., "Synthesis of intermediates for the lactone moiety of mevinic acids via tellurium chemistry", J. Org. Chem., (1994) 59(17):4760-4764.
Kusakabe et al., "Preparation of Optically Acitve 2-Furylcarbinols by Kinetic Resolution Using the Sharpless Reagent and Their Application in Organic Synthesis", J org Chem (1989) 54(9):2085-2091.
Laitar et al., "Catalytic diboration of aldehydes via insertion into the copper-boron bond", J Am Chem Soc. (2006) 128(34):11036-11037.
Li et al, "Novel macrocyclic HCV NS3 protease inhibitors derived from α-amino cyclic boronates", Bioorganic Med Chem Lett. (2010) 20:5695-5700.
Li et al., "Synthesis and evaluation of novel alpha-amino cyclic boronates as inhibitors of HCV NS3 protease", Bioorg Med Chem Lett. (2010) 20:3550-3556.
Li et al., "Stereoselective total synthesis of etnangien and etnangien methyl ester", J Org Chem. (2010) 75(8):2429-2444.
Liang et al., "The Efficient Copper(I) (Hexabenzyl)tren Catalyst and Dendritic Analogues for Green "Click" Reactions between Azides and Alkynes in Organic Solvent and in Water: Positive Dendritic Effects and Monometallic Mechanism", Advance Syn Catal. (2011) 353(18): 3434-3450.
Liu et al., "Selective Protein tyrosine phosphatase 1B inhibitors: Targeting the second phosphotyrosine binding site with non-carboxylic acid-containing ligands", J Med Chem. (2003) 46(16):3437-3440.
Liu et al., "Application of Stereoselective Ether Transfer to the Synthesis of Isotactic Polyethers", J Org Chem. (2010) 75(12):3953-3957.
Livermore et al., "Activities of NXL104 combinations with Ceftazidime and Aztreonam against Carbapenemase-producing Enterobacteriaceae", Antimicr Agents Chemother. (2011) 55(1):390-394.
Matteson et al., "Iodomethaneboronic Esters and Aminomethaneboronic Esters", J Organomet. Chem. (1979) 170:259-264.
Matteson et al., "A Directed Chiral Synthesis of Amino Acids from Boronic Esters", Tetrahedron Lett. (1987) 28(39):4499-4502.
Matteson, D.S., "Asymmetric Synthesis with Boronic Esters", Acc Chem Res. (1988) 21(8):294-300.
Matteson, "Boronic esters in stereodirected synthesis", Tetrahedron (1989) 45(7):1859-1885.
Matteson et al., "A stereospecific convergent coupling of nucleophilic and electrophilic chiral carbons", J. Am. Chem. Soc. (1989) 111:4399-4402.

Matteson et al., "Synthesis of asymmetrically deuterated glycerol and dibenzylglyceraldehyde via boronic esters", J. Am. Chem. Soc. (1990) 112:3964-3969.
Matteson et al., "(Alkoxyalkyl)boronic Ester Intermediates for Asymmetric Synthesis", Organometallics (1996) 15:152-163.
Matteson, "Alpha-Halo Baronic Esters in Asymmetric Synthesis", Tetrahedron (1998) 54(36):10555-10607.
Matteson et al., "Synthesis of a (Beta-acetamido-alpha-acetoxyethyl) boronic ester via azido boronic esters", J Organomet Chem. (2008) 693:2258-2262.
Meanwell, "Synopsis of some recent tactical application of bioisosteres in drug design", J. Med. Chem. (2011) 54:2529-2591.
Micalizio et al., "A Boronic Ester Annulation Strategy for Diversity-Oriented Organic Synthesis", Angew Chem Int Ed Engl. (2002) 41(1):152-154.
Montalbetti et al., "Amide bond formation and peptide coupling", Tetrahedron (2005) 61:10827-10852.
Montefour et al., "*Acinetobacter baumannii*: an emerging multidrug-resistant pathogen in critical care", Crit Care Nurse (2008) 28(1):15-25.
Morandi et al., "Structure-based optimization of cephalothin-analogue boronic acids as beta-lactamase inhibitors", Bioorg Med Chem. (2008) 16(3):1195-205. Epub Nov. 7, 2007.
Nema et al., "Excipients and Their Role in Approved Injectable Products: Current Usage and Future Directions", PDA J Pharm Sci Technol. (2011) 65(3):287-332.
Ness et al., "Structure-based design guides the improved efficacy of deacylation transition state analogue inhibitors of TEM-1 beta-Lactamase", Biochemistry (2000) 39(18):5312-5321.
Nordmann et al., How to Detect NDM-1 Producers, J. Clin. Micro. (2011) 49:718-721.
Panek et al., "Diastereoselectivity in the borane methyl sulfide promoted hydroboration of .alpha.-alkoxy-.beta, gamma.-unsaturated esters. Documentation of an alkoxy-directed hydroboration reaction", J. Org. Chem. (1992) 57(20):5288-5290.
Paterson et al., "Extended-Spectrum beta-Lactamases: a Clinical Update", Clin Microbiol Rev. (2005) 18(4):657-686.
Perez et al., "Why are we afraid of *Acinetobacter baumannii*?", Expert Rev Anti Infect Ther. (2008) 6(3):269-71.
Pintaric et al., "An Opportunity for Mg-Catalyzed Grignard-Type Reactions: Direct Coupling of Benzylic Halides with Pinacolborane with 10 mol % of Magnesium", J Am Chem Soc. (2010) 132(34): 11825-11827.
Powell et al., "Compendium of excipients for parenteral formulations", PDA J Pharm Sci Technol. (1998) 52(5):238-311.
Reissig et al.,"High diastereoselection in the alkylation of siloxy-substituted methyl cyclopropanecarboxylates: consequence of a pyramidal ester enolate anion?", J. Am. Chem. Soc. (1982) 104:1735-1737.
Robak et al., "Synthesis and applications of tert-butanesulfinamide", Chem Rev. (2010) 110(6):3600-3740.
Rodriguez-Martinez et al., "VIM-19, a Metallo-beta-lactamase with increased Carbapenemase Activity from *Escherichia coli* and *Klebsiella pneumoniae*", Antimicro Agents Chemother. (2010) 54(1):471-476.
Sawyer et al., "Physical properties and synthetic utility of a-alkoxyorganolithium species as studied through ligand selectivity in tin-lithium exchange", J. Am. Chem. Soc. (1988) 110:842-853.
Selander et al., "Palladium-catalyzed allylic C-OH functionalization for efficient synthesis of functionalized allylsilanes", J Am Chem Soc. (2011) 133(3):409-411.
Shaffer, Robyn Kroop, "The Challenge of Antibiotic-Resistant *Staphylococcus*: Lessons from Hospital Nurseries in the mid-20th Century", Yale J Biol Med. (2013) 86:261-270.
Shao et al., "Asymmetric hydrogenation of 3,5-Dioxoesters catalyzed by Ru-binap complex: A short step asymmetric synthesis of 6-substituted 5,6-dehydro-2-pyrones", Tetrahedron (1993) 49(10):1997-2010.
Singh et al., "Assymetric Homologation of Boronic Esters Bearing Azido and Silyloxy Substituents", J Org Chem (2000) 65(20):6650-6653 and Erratum: J Org Chem. (2001) 66(22):7560.
Sliwka et al., "Synthetic Sulfur Carotenoids II: Optically Active Carotenoid Thiols", Tetrahedron: Asymmetry (1993) 4(3):361-368.

(56) References Cited

OTHER PUBLICATIONS

Solladié et al., "First Stereocontrolled Synthesis of the (3S,5R,7R,10R,11R)-C1-C13 Fragment of Nystatin A(1)", J Org Chem. (1999) 64(15):5447-5452.

Souto et al., "Synthesis and biological characterization of the histone deacetylase inhibitor largazole and c7-modified analogues", J. Med. Chem. (2010) 53(12):4654-4667.

Spiegel et al., "CP-263,114 synthetic studies. Construction of an isotwistane ring system via rhodium carbenoid C-H insertion", Tetrahedron (2002) 58:6545-6554.

Teo et al., "Efficient and highly aldehyde selective Wacker oxidation", Org Lett. (2012) 14(13):3237-3239.

Theuretzbacher et al., "Update on antibacterial and antifungal drugs—can we master the resistance crisis?", Curr Opin Pharmacol. (2011) 11:429-432.

Vasil'Ev et al., (1977): STN International HCAPLUS database, Columbus (OH), accession No. 1977: 72730; 1 page.

Vitor et al., "Rhenium(I)-and technetium(I) tricarbonyl complexes anchored by bifunctional pyrazole-diamine and pyrazole-dithioether chelators", J Organometal Chem (2004) 689(25):4764-4774.

Waley, Stephen G., "A quick method for the determination of inhibition constants", Biochem J. (1982) 205(3):631-633.

Walsh et al., "Metallo-beta-Lactamases: the Quiet before the Storm?", Clin Microbiol Rev. (2005) 18(2):306-325.

Wang et al., "Recognition and resistance in TEM beta-lactamase", Biochemistry (2003) 42(28):8434-8444.

Wohlrab et al., "Total synthesis of plusbacin A3: a depsipeptide antibiotic active against vancomycin-resistant bacteria", J. Am. Chem. Soc. (2007) 129:4175-4177.

Xia et al., "Synthesis and SAR of novel benzoxaboroles as a new class of beta-lactamase inhibitors", Bioorg Med Chem Lett. (2011) 21:2533-2536.

Yamamoto et al., "Iridium-catalyzed hydroboration of alkenes with pinacolborane", Tetrahedron (2004) 60:10695-10700.

Yanagisawa et al., "Nonpeptide angiotensin II receptor antagonists: synthesis, biological activities, and structure-activity relationships of imidazole-5-carboxylic acids bearing alkyl, alkenyl, and hydroxyalkyl substituents at the 4-position and their related compounds", J Med Chem. (1996) 39(1):323-338.

Yuen et al., "Deprotection of pinacolyl boronate esters via hydrolysis of intermediate potassium trifluoroborates", Tetrahed Lttr. (2005)46(46):7899-7903.

International Search Report and Written Opinion dated Sep. 14, 2011 for International Patent Application No. PCT/US2011/046957, filed Aug. 8, 2011.

International Search Report and Written Opinion dated Nov. 5, 2012 for International Patent Application No. PCT/US2012/053233, filed Aug. 30, 2012.

International Search Report and Written Opinion dated May 9, 2013 for International Patent Application No. PCT/US2013/025621, filed Feb. 11, 2013.

International Search Report and Written Opinion dated Aug. 29, 2013 for International Application No. PCT/US2013/044377, filed Jun. 5, 2013.

International Search Report and Written Opinion dated Mar. 12, 2014 for International Patent Application No. PCT/US2014/010106, filed Jan. 2, 2014.

International Search Report and Written Opinion dated Mar. 12, 2014 for International Patent Application No. PCT/US2014/010107, filed Jan. 2, 2014.

U.S. Office Action, mailed Aug. 20, 2013, in co-pending/related U.S. Appl. No. 13/205,112.

U.S. Office Action, mailed Apr. 1, 2014, in co-pending/related U.S. Appl. No. 13/898,959.

Chemicalland21.com. "Meglumine", Jun. 7, 2011. Downloaded from </www.chemicalland21.com/lifescience/phar/N-METHYL-D-GLUCAMINE.htm>.

Danziger et al., "Automated Site-directed Drug Design: A General Algorithm for Knowledge Acquisition about Hydrogen-bonding Regions at Protein Surfaces", Proc. Royal Soc London, Series B, Biol. Sciences (1989) 236(1283):101-113.

* cited by examiner

HETEROCYCLIC BORONIC ACID ESTER DERIVATIVES AND THERAPEUTIC USES THEREOF

RELATED APPLICATIONS

This application is the U.S. National Phase of Application No. PCT/US2012/053233 entitled "HETEROCYCLIC BORONIC ACID ESTER DERIVATIVES AND THERAPEUTIC USES THEREOF" filed Aug. 30, 2012 and published in English on Mar. 7, 2013 as WO 2013/033461 which claims the benefit of U.S. Provisional Application No. 61/529,859 filed Aug. 31, 2011, which is incorporated herein by reference in its entirety.

FIELD OF THE INVENTION

The present invention relates to antimicrobial compounds, compositions, their use and preparation as therapeutic agents. In particular, the present invention relates to cyclic boronate compounds.

BACKGROUND OF THE INVENTION

Antibiotics have been effective tools in the treatment of infectious diseases during the last half-century. From the development of antibiotic therapy to the late 1980s there was almost complete control over bacterial infections in developed countries. However, in response to the pressure of antibiotic usage, multiple resistance mechanisms have become widespread and are threatening the clinical utility of antibacterial therapy. The increase in antibiotic resistant strains has been particularly common in major hospitals and care centers. The consequences of the increase in resistant strains include higher morbidity and mortality, longer patient hospitalization, and an increase in treatment costs Various bacteria have evolved β-lactam deactivating enzymes, namely, β-lactamases, that counter the efficacy of the various β-lactams. β-lactamases can be grouped into 4 classes based on their amino acid sequences, namely, Ambler classes A, B, C, and D. Enzymes in classes A, C, and D include active-site serine β-lactamases, and class B enzymes, which are encountered less frequently, are Zn-dependent. These enzymes catalyze the chemical degradation of β-lactam antibiotics, rendering them inactive. Some β-lactamases can be transferred within and between various bacterial strains and species. The rapid spread of bacterial resistance and the evolution of multi-resistant strains severely limits β-lactam treatment options available.

The increase of class D β-lactamase-expressing bacterium strains such as *Acinetobacter baumannii* has become an emerging multidrug-resistant threat. *A. baumannii* strains express A, C, and D class β-lactamases. The class D β-lactamases such as the OXA families are particularly effective at destroying carbapenem type β-lactam antibiotics, e.g., imipenem, the active carbapenems component of Merck's Primaxin® (Montefour, K.; et al. Crit. Care Nurse 2008, 28, 15; Perez, F. et al. Expert Rev. Anti Infect. Ther. 2008, 6, 269; Bou, G.; Martinez-Beltran, J. Antimicrob. Agents Chemother. 2000, 40, 428. 2006, 50, 2280; Bou, G. et al, J. Antimicrob. Agents Chemother. 2000, 44, 1556). This has imposed a pressing threat to the effective use of drugs in that category to treat and prevent bacterial infections. Indeed the number of catalogued serine-based β-lactamases has exploded from less than ten in the 1970s to over 300 variants. These issues fostered the development of five "generations" of cephalosporins. When initially released into clinical practice, extended-spectrum cephalosporins resisted hydrolysis by the prevalent class A β-lactamases, TEM-1 and SHV-1. However, the development of resistant strains by the evolution of single amino acid substitutions in TEM-1 and SHV-1 resulted in the emergence of the extended-spectrum β-lactamase (ESBL) phenotype.

New β-lactamases have recently evolved that hydrolyze the carbapenem class of antimicrobials, including imipenem, biapenem, doripenem, meropenem, and ertapenem, as well as other β-lactam antibiotics. These carbapenemases belong to molecular classes A, B, and D. Class A carbapenemases of the KPC-type predominantly in *Klebsiella pneumoniae* but now also reported in other Enterobacteriaceae, *Pseudomonas aeruginosa* and *Acinetobacter baumannii*. The KPC carbapenemase was first described in 1996 in North Carolina, but since then has disseminated widely in the US. It has been particularly problematic in the New York City area, where several reports of spread within major hospitals and patient morbidity have been reported. These enzymes have also been recently reported in France, Greece, Sweden, United Kingdom, and an outbreak in Germany has recently been reported. Treatment of resistant strains with carbapenems can be associated with poor outcomes.

Another mechanism of β-lactamase mediated resistance to carbapenems involves combination of permeability or efflux mechanisms combined with hyper production of β-lactamases. One example is the loss of a porin combined in hyperproduction of ampC β-lactamase results in resistance to imipenem in *Pseudomonas aeruginosa*. Efflux pump over expression combined with hyperproduction of the ampC β-lactamase can also result in resistance to a carbapenem such as meropenem.

Thus, there is a need for improved β-lactamase inhibitors.

SUMMARY OF THE INVENTION

The present invention relates to antimicrobial agents. Some embodiments include compounds, compositions, pharmaceutical compositions, use and preparation thereof. In particular, some embodiments, relate to cyclic boronate derivatives.

Some embodiments include compounds having the structure of formula I:

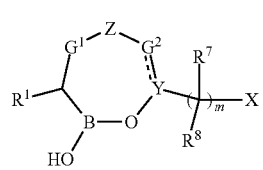

or pharmaceutically acceptable salt thereof, wherein:

$R^1$ is selected from a group consisting of —$C_{1-9}$alkyl, —$C_{2-9}$alkenyl, —$C_{2-9}$alkynyl, —$NR^9R^{10}$, —$C_{1-9}$alkyl$R^{11}$, —$C_{2-9}$alkenyl$R^{11}$, —$C_{2-9}$alkynyl$R^{11}$, -carbo cyclyl-$R^{11}$, —CH(OH)$C_{1-9}$alkyl$R^9$, —CH(OH)$C_{2-9}$alkenyl$R^9$, —CH(OH)$C_{2-9}$alkynyl$R^9$, —CH(OH)carbocyclyl-$R^9$, —C(=O)$R^9$, —C(=O)$C_{1-9}$alkyl$R^9$, —C(=O)$C_{2-9}$alkenyl$R^9$, —C(=O)$C_{2-9}$alkynyl$R^9$, —C(=O)carbocyclyl-$R^9$, —C(=O)$NR^9R^{10}$, —N($R^9$)C(=O)$R^9$, —N($R^9$)C(=O)$NR^9R^{10}$, —N($R^9$)C(=O)$OR^9$, —N($R^9$)C(=O)C(=$NR^{10}$)$R^9$, —N($R^9$)C(=O)C(=$CR^9R^{10}$)$R^9$, —N($R^9$)C(=O), $C_{1-4}$alkylN($R^9$)C(=O)$R^9$, —N($R^9$)C(=$NR^{10}$)$R^9$, —C(=$NR^{10}$)$NR^9R^{10}$, —N=C($R^9$)$NR^9R^{10}$, —N($R^9$)$SO_2R^9$, —N($R^9$)$SO_2NR^9R^{10}$, —N=CHR$^9$, —C($R^9R^{10}$)C (=O)NR⁹R¹⁰, —C(R⁹R¹⁰)N(R⁹)C(=O)R⁹, —C(R⁹R¹⁰)OR⁹, substituted or unsubstituted aryl, substituted or unsubstituted heteroaryl, substituted or unsubstituted carbocyclyl, and substituted or unsubstituted heterocyclyl;

G¹ is selected from a divalent group consisting of —C(RᵃRᵇ)—, —C(RᵃRᵇ)C(RᶜRᵈ)—, —C(Rᵃ)=C(Rᶜ)—, —C(=O)C(RᵃRᵇ)—, —C(RᵃRᵇ)C(=O)—, and a bond;

G² is selected from a divalent group consisting of —C(RᵉRᶠ)—, —C(=Rᵉ')—, =C(Rᵉ)—, —C(RᵉRᶠ)C(RᵍRʰ)—, —C(RᵉRᶠ)C(RᵍRʰ)C(RⁱRʲ)—, —C(=O)—, —C(=O)C(RᵉRᶠ)—, —C(RᵉRᶠ)C(=O)—, —C(=O)C(RᵉRᶠ)C(RᵍRʰ)—, —C(RᵉRᶠ)C(RᵍRʰ)C(=O)—, —C(=O)C(RᵉRᶠ)C(RᵍRʰ)C(RⁱRʲ)—, —C(RᵉRᶠ)C(RᵍRʰ)C(RⁱRʲ)C(=O)—, —C(Rᵉ)=C(Rᵍ)—, —C(Rᵉ)=C(Rᵍ)C(RⁱRʲ)— and —C(RᵉRᶠ)C(Rᵍ)=C(Rʲ)—;

Rᵃ, Rᵇ, Rᶜ, Rᵈ, Rᵉ, Rᶠ, Rᵍ, Rʰ, Rⁱ, and Rʲ are independently selected from a group consisting of H, Cl, F, CN, CF₃, —R⁹, —OR⁹, NR⁹R¹⁰, —C(=O)NR⁹R¹⁰, and —C(=O)OR⁹, or independently: Rᵃ and Rᶜ, Rᵉ and an R⁷, Rᵉ and R⁶, Rᵃ and R⁷, Rᵏ and Rᶜ, Rᵏ and Rᵉ, Rᵉ and Rᵍ, and Rᵍ and Rʲ are taken together with the atoms to which they are attached and any intervening atoms to form a substituted or unsubstituted aryl, substituted or unsubstituted heteroaryl, substituted or unsubstituted carbocyclyl or substituted or unsubstituted heterocyclyl, or independently Rᵉ and Rᶠ are taken together with the atoms to which they are attached and any intervening atoms to form a substituted or unsubstituted carbocyclyl or substituted or unsubstituted heterocyclyl;

Rᵃ' and Rᵉ' are =CR⁹R¹⁰ or independently Rᵃ' and Rᵏ, or Rᵉ' and Rᵏ, are taken together with the atoms to which they are attached to form a substituted or unsubstituted aryl, substituted or unsubstituted heteroaryl, substituted or unsubstituted carbocyclyl, or substituted or unsubstituted heterocyclyl;

Z is selected from a divalent group consisting of —C(R⁹R¹⁰)—, —O—, —S—, —N(R⁹)—, —N[C(=O)R⁹]—, —N[C(=O)NR⁹R¹⁰]—, —N[C(=O)OR⁹]—, —N[C(=NR¹⁰)R⁹]—, —N[SO₂R⁹]—, —N[SO₂NR⁹R¹⁰]—, —N(R⁹)C(=O)—, —C(R⁹Rᵏ)—, —C(=Rᵏ)—, —N(Rᵏ)—, and a bond;

Rᵏ and Rᵉ, Rᵏ and Rᵉ, Rᵃ' and Rᵏ, or Rᵉ' and Rᵏ are taken together with any intervening atoms to form a substituted or unsubstituted aryl, substituted or unsubstituted heteroaryl, substituted or unsubstituted carbocyclyl or substituted or unsubstituted heterocyclyl;

Y is selected from a group consisting of N, CR⁶, and C, with the proviso that when Z is a bond, —C(R⁹R¹⁰)—, —C(R⁹Rᵏ)—, or —C(=Rᵏ)—, then Y is N;

R⁶ is selected from a group consisting of H, —C₂₋₉alkenyl, —C₂₋₉alkynyl, carbocyclyl, —C₁₋₉alkylR¹¹, —C₂₋₉alkenylR¹¹, —C₂₋₉alkynylR¹¹, carbocyclyl-R¹¹, —C(=O)OR⁹ and —C₁₋₉alkylCO₂R⁹, —C₂₋₉alkenylCO₂R⁹, —C₂₋₉alkynylCO₂R⁹, and -carbocyclyl-CO₂R⁹, or alternatively R⁶ and an R⁷ or R⁶ and Rᵉ are taken together with the atoms to which they are attached and any intervening atoms to form a substituted or unsubstituted carbocyclyl or substituted or unsubstituted heterocyclyl;

each R⁷ is independently selected from a group consisting of H, halo, —C₁₋₉alkyl, —C₂₋₉alkenyl, —C₂₋₉alkynyl, —NR⁹R¹⁰, —OR⁹, —C₁₋₉alkylCO₂R⁹, —C₂₋₉alkenylCO₂R⁹, —C₂₋₉alkynylCO₂R⁹, and -carbocyclyl-CO₂R⁹, or independently, R⁶ and an R⁷ or an R⁷ and an R⁸ are taken together with the atoms to which they are attached and any intervening atoms to form a substituted or unsubstituted carbocyclyl or substituted or unsubstituted heterocyclyl, or independently an R⁷ and Rᵉ are taken together with intervening atoms to form a substituted or unsubstituted aryl, substituted or unsubstituted heteroaryl, substituted or unsubstituted carbocyclyl, or substituted or unsubstituted heterocyclyl;

each R⁸ is independently selected from a group consisting of H, halo, —C₁₋₉alkyl, —C₂₋₉alkenyl, —C₂₋₉alkynyl, —NR⁹R¹⁰, —OR⁹, —C₁₋₉alkylCO₂R⁹, —C₁₋₉alkylCO₂R⁹, —C₂₋₉alkenylCO₂R⁹, —C₂₋₉alkynylCO₂R⁹, and -carbocyclyl-CO₂R⁹, or independently, an R⁷ and an R⁸ are taken together with the atoms to which they are attached to form a substituted or unsubstituted carbocyclyl or substituted or unsubstituted heterocyclyl, or independently, each R⁸ attached to a ring atom forming part of a substituted or unsubstituted aryl or a substituted or unsubstituted heteroaryl is absent;

each R⁹ is independently selected from a group consisting of H, —C₁₋₉alkyl, C₂₋₉alkenyl, —C₂₋₉alkynyl, carbocyclyl, —C₁₋₉alkylR¹¹, C₂₋₉alkenylR¹¹, —C₂₋₉alkynylR¹¹, -carbocyclyl-R¹¹, —C₁₋₉alkylCO₂R¹², C₂₋₉alkenylCO₂R¹², —C₂₋₉alkynylCO₂R¹², -carbocyclylCO₂R¹², —C₁₋₉alkyl-N(R¹²)OR¹², C₂₋₉alkenyl-N(R¹²)OR¹², —C₂₋₉alkynyl-N(R¹²)OR¹², -carbocyclyl-N(R¹²)OR¹², —C₁₋₉alkyl-OR¹², C₂₋₉alkenyl-OR¹², —C₂₋₉alkynyl-OR¹², -carbocyclyl-OR¹², substituted or unsubstituted aryl, substituted or unsubstituted heteroaryl, substituted or unsubstituted carbocyclyl, and substituted or unsubstituted heterocyclyl;

each R¹⁰ is independently selected from a group consisting of H, —C₁₋₉alkyl, —OR⁹, —CH(=NH)—, —C(=O)R⁹, substituted or unsubstituted aryl, substituted or unsubstituted heteroaryl, substituted or unsubstituted carbocyclyl, and substituted or unsubstituted heterocyclyl;

each R¹¹ is independently selected from a group consisting of substituted or unsubstituted aryl, substituted or unsubstituted heteroaryl, substituted or unsubstituted carbocyclyl, and substituted or unsubstituted heterocyclyl;

each R¹² is independently selected from a group consisting of H, C₁₋₉alkyl, —(CH₂)₀₋₃—R₁₁, —C(R¹³)₂OC(O)C₁₋₉alkyl, —C(R¹³)₂OC(O)R¹¹, —C(R¹³)₂OC(O)OC₁₋₉alkyl and —C(R¹³)₂OC(O)OR¹¹;

each R¹³ is independently selected from a group consisting of H and C₁₋₄alkyl;

each X is independently selected from a group consisting of H, —CO₂R¹², and carboxylic acid isosteres;

m is independently zero or an integer from 1 to 2;

the bond represented by a dashed and solid line represents a bond selected from the group consisting of a single bond and a double bond; and each C₁₋₉alkyl, C₂₋₉alkenyl, and C₂₋₉alkynyl is optionally substituted.

Some embodiments include compounds having the defined stereochemistry at 3-position shown in formula Ia:

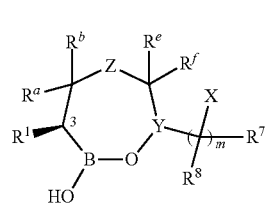

Ia

Some embodiments wherein Y is CR⁶ include compounds having the defined 3,7-trans-stereochemistry shown in formula Ib:

Some embodiments wherein Y is $CR^6$ include compounds having the defined 3,7-cis-stereochemistry shown in formula Ic:

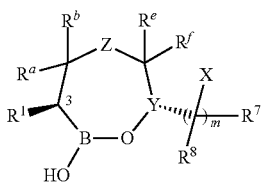

Ib

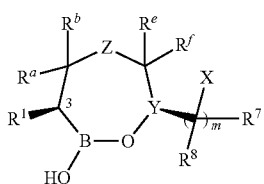

Ic

In addition to the foregoing, some embodiments include a pharmaceutical composition comprising a therapeutically effective amount of any one of the foregoing compounds or a pharmaceutically acceptable salt thereof and a pharmaceutically acceptable excipient.

In addition to the foregoing, some embodiments include any one of the foregoing compounds or compositions for the treatment or prevention of a bacterial infection.

In addition to the foregoing, some embodiments include methods for treating or preventing a bacterial infection comprising administering to a subject in need thereof, an effective amount of any one of the foregoing compounds or compositions.

Some embodiments further comprise administering an additional medicament.

In addition to the foregoing, some embodiments include the use of any one of the foregoing compounds or compositions in the preparation of a medicament for the treatment or prevention of a bacterial infection.

In some embodiments, the use of any one of the foregoing compounds or compositions, further comprises the use of an additional medicament for treating or preventing a bacterial infection.

In some embodiments, the additional medicament includes an antibacterial agent, antifungal agent, an antiviral agent, an anti-inflammatory agent or an anti-allergic agent.

In some embodiments, the additional medicament comprises an antibacterial agent such as a β-lactam.

In some embodiments, the β-lactam includes Amoxicillin, Ampicillin (Pivampicillin, Hetacillin, Bacampicillin, Metampicillin, Talampicillin), Epicillin, Carbenicillin (Carindacillin), Ticarcillin, Temocillin, Azlocillin, Piperacillin, Mezlocillin, Mecillinam (Pivmecillinam), Sulbenicillin, Benzylpenicillin (G), Clometocillin, Benzathine benzylpenicillin, Procaine benzylpenicillin, Azidocillin, Penamecillin, Phenoxymethylpenicillin (V), Propicillin, Benzathine phenoxymethylpenicillin, Pheneticillin, Cloxacillin (Dicloxacillin, Flucloxacillin), Oxacillin, Meticillin, Nafcillin, Faropenem, Biapenem, Doripenem, Ertapenem, Imipenem, Meropenem, Panipenem, Cefazolin, Cefacetrile, Cefadroxil, Cefalexin, Cefaloglycin, Cefalonium, Cefaloridine, Cefalotin, Cefapirin, Cefatrizine, Cefazedone, Cefazaflur, Cefradine, Cefroxadine, Ceftezole, Cefaclor, Cefamandole, Cefminox, Cefonicid, Ceforanide, Cefotiam, Cefprozil, Cefbuperazone, Cefuroxime, Cefuzonam, Cefoxitin, Cefotetan, Cefmetazole, Loracarbef, Cefixime, Ceftazidime, Ceftriaxone, Cefcapene, Cefdaloxime, Cefdinir, Cefditoren, Cefetamet, Cefinenoxime, Cefodizime, Cefoperazone, Cefotaxime, Cefpimizole, Cefpiramide, Cefpodoxime, Cefsulodin, Cefteram, Ceftibuten, Ceftiolene, Ceftizoxime, Flomoxef, Latamoxef, Cefepime, Cefozopran, Cefpirome, Cefquinome, Ceftobiprole, Ceftaroline, Ceftiofur, Cefquinome, Cefovecin, Aztreonam, Tigemonam or Carumonam.

In some embodiments, the β-lactam includes Ceftazidime, Biapenem, Doripenem, Ertapenem, Imipenem, Meropenem or Panipenem.

In some embodiments, the β-lactam includes Aztreonam, Tigemonam or Carumonam.

In some embodiments, the subject is a mammal.

In some embodiments, the mammal is a human.

In some embodiments, the infection comprises a bacteria that includes *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia* group, *Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Acinetobacter anitratisYersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis,* or *Staphylococcus saccharolyticus.*

In some embodiments, the infection comprises a bacteria that includes *Pseudomonas aeruginosa, Pseudomonas fluorescens, Stenotrophomonas maltophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Acinetobacter calcoaceticus, Acinetobacter haemolyticus, Yersinia entero-* colitica, Yersinia pestis, Yersinia pseudotuberculosis, Yersinia intermedia, Haemophilus influenzae, Haemophilus parainfluenzae, Haemophilus haemolyticus, Haemophilus parahaemolyticus, Helicobacter pylori, Campylobacter fetus, Campylobacter jejuni, Campylobacter coli, Vibrio cholerae, Vibrio parahaemolyticus, Legionella pneumophila, Listeria monocytogenes, Neisseria gonorrhoeae, Neisseria meningitidis, Moraxella, Bacteroides fragilis, Bacteroides vulgatus, Bacteroides ovalus, Bacteroides thetaiotaomicron, Bacteroides uniformis, Bacteroides eggerthii, or Bacteroides splanchnicus.

DETAILED DESCRIPTION

The present invention relates to antimicrobial agents and potentiators thereof. Some embodiments include compounds, compositions, pharmaceutical compositions, uses thereof, including methods of preparation, and methods of treatment. In particular, the present invention relates to cyclic boronate derivatives. Some embodiments of the present invention include compounds of formula (I):

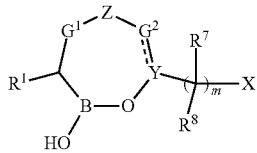

I or pharmaceutically acceptable salts thereof.

In some embodiments, $R^1$ is selected from a group consisting of $-C_{1-9}$alkyl, $-C_{2-9}$alkenyl, $-C_{2-9}$alkynyl, $-NR^9R^{10}$, $-C_{1-9}$alkyl$R^{11}$, $-C_{2-9}$alkenyl$R^{11}$, $-C_{2-9}$alkynyl$R^{11}$, -carbocyclyl-$R^{11}$, $-CH(OH)C_{1-9}$alkyl$R^9$, $-CH(OH)C_{2-9}$alkenyl$R^9$, $-CH(OH)C_{2-9}$alkynyl$R^9$, $-CH(OH)$carbocyclyl-$R^9$, $-C(=O)R^9$, $-C(=O)C_{1-9}$alkyl$R^9$, $-C(=O)C_{2-9}$alkenyl$R^9$, $-C(=O)C_{2-9}$alkynyl$R^9$, $-C(=O)$carbocyclyl-$R^9$, $-C(=O)NR^9R^{10}$, $-N(R^9)C(=O)R^9$, $-N(R^9)C(=O)NR^9R^{10}$, $-N(R^9)C(=O)OR^9$, $-N(R^9)C(=O)C(=NR^{10})R^9$, $-N(R^9)C(=O)C(=CR^9R^{10})R^9$, $-N(R^9)C(=O)C_{1-4}$alkyl$N(R^9)C(=O)R^9$, $-N(R^9)C(=NR^{10})R^9$, $-C(=NR^{10})NR^9R^{10}$, $-N=C(R^9)NR^9R^{10}$, $-N(R^9)SO_2R^9$, $-N(R^9)SO_2NR^9R^{10}$, $-N=CHR^9$, $-C(R^9R^{10})C(=O)NR^9R^{10}$, $-C(R^9R^{10})N(R^9)C(=O)R^9$, $-C(R^9R^{10})OR^9$, substituted or unsubstituted aryl, substituted or unsubstituted heteroaryl, substituted or unsubstituted carbocyclyl, and substituted or unsubstituted heterocyclyl.

In some embodiments, $G^1$ is selected from a divalent group consisting of $-C(R^aR^b)-$, $-C(=R^{a\prime})-$, $-C(R^aR^b)C(R^cR^d)-$, $-C(R^a)=C(R^c)-$, $-C(=O)C(R^aR^b)-$, $-C(R^aR^b)C(=O)-$, and a bond.

In some embodiments, $G^2$ is selected from a divalent group consisting of $-C(R^eR^f)-$, $-C(=R^{e\prime})-$, $=C(R^e)-$, $-C(R^eR^f)C(R^gR^h)-$, $-C(R^eR^f)C(R^gR^h)C(R^iR^j)-$, $-C(=O)-$, $-C(=O)C(R^eR^f)-$, $-C(R^eR^f)C(=O)-$, $-C(=O)C(R^eR^f)C(R^gR^h)-$, $-C(R^eR^f)C(R^gR^h)C(=O)-$, $-C(=O)C(R^eR^f)C(R^gR^h)C(R^iR^j)-$, $-C(R^eR^f)C(R^gR^h)C(R^iR^j)C(=O)-$, $-C(R^e)=C(R^g)-$, $-C(R^e)=C(R^g)C(R^iR^j)-$ and $-C(R^eR^f)C(R^g)=C(R^j)-$.

In some embodiments, $R^a$, $R^b$, $R^c$, $R^d$, $R^e$, $R^f$, $R^g$, $R^h$, $R^i$, and $R^j$ are independently selected from a group consisting of H, Cl, F, CN, $CF_3$, $-R^9$, $-OR^9$, $NR^9R^{10}$, $-C(=O)NR^9R^{10}$, and $-C(=O)OR^9$, or independently: $R^a$ and $R^c$, $R^e$ and an $R^7$, $R^e$ and $R^6$, $R^k$ and $R^cR^k$ and $R^e$, $R^e$ and $R^g$, and $R^g$ and $R^j$ are taken together with the atoms to which they are attached and any intervening atoms to form a substituted or unsubstituted aryl, substituted or unsubstituted heteroaryl, substituted or unsubstituted carbocyclyl or substituted or unsubstituted heterocyclyl, or independently $R^e$ and $R^f$ are taken together with the atoms to which they are attached and any intervening atoms to form a substituted or unsubstituted carbocyclyl or substituted or unsubstituted heterocyclyl.

In some embodiments, $R^{a\prime}$ and $R^{e\prime}$ are $=CR^9R^{10}$ or independently $R^{a\prime}$ and $R^k$, or $R^{e\prime}$ and $R^k$, are taken together with the atoms to which they are attached to form a substituted or unsubstituted aryl, substituted or unsubstituted heteroaryl, substituted or unsubstituted carbocyclyl, or substituted or unsubstituted heterocyclyl.

In some embodiments, Z is selected from a divalent group consisting of $-C(R^9R^{10})-$, $-O-$, $-S-$, $-N(R^9)-$, $-N[C(=O)R^9]-$, $-N[C(=O)NR^9R^{10}]-$, $-N[C(=O)OR^9]-$, $-N[C(=NR^{10})R^9]-$, $-N[SO_2R^9]-$, $-N[SO_2NR^9R^{10}]-$, $-N(R^9)C(=O)-$, $-C(R^9R^k)-$, $-C(=R^k)-$, $-N(R^k)-$, and a bond.

In some embodiments, $R^k$ and $R^e$, $R^k$ and $R^e$, $R^{a\prime}$ and $R^k$, or $R^{e\prime}$ and $R^k$ are taken together with any intervening atoms to form a substituted or unsubstituted aryl, substituted or unsubstituted heteroaryl, substituted or unsubstituted carbocyclyl or substituted or unsubstituted heterocyclyl.

In some embodiments, Y is selected from a group consisting of N, $CR^6$, and C.

In some embodiments, when Z is a bond, $-C(R^9R^{10})-$, $-C(R^9R^k)-$, or $-C(=R^k)-$, then Y is N.

In some embodiments, $R^6$ is selected from a group consisting of H, $-C_{1-9}$alkyl, $-C_{2-9}$alkenyl, $-C_{2-9}$alkynyl, carbocyclyl, $-C_{1-9}$alkyl$R^{11}$, $-C_{2-9}$alkenyl$R^{11}$, $-C_{2-9}$alkynyl$R^{11}$, carbocyclyl-$R^{11}$, $-C(=O)OR^9$ and $-C_{1-9}$alkyl$CO_2R^9$, $-C_{2-9}$alkenyl$CO_2R^9$, $-C_{2-9}$alkynyl$CO_2R^9$, and -carbocyclyl-$CO_2R^9$, or alternatively $R^6$ and an $R^7$ or $R^6$ and $R^e$ are taken together with the atoms to which they are attached and any intervening atoms to form a substituted or unsubstituted carbocyclyl or substituted or unsubstituted heterocyclyl.

In some embodiments, each $R^7$ is independently selected from a group consisting of H, halo, $-C_{1-9}$alkyl, $-C_{2-9}$alkenyl, $-C_{2-9}$alkynyl, $-NR^9R^{10}$, $-OR^9$, $-C_{1-9}$alkyl$CO_2R^9$, $-C_{2-9}$alkenyl$CO_2R^9$, $-C_{2-9}$alkynyl$CO_2R^9$, and -carbocyclyl-$CO_2R^9$, or independently, $R^6$ and an $R^7$ or an $R^7$ and an $R^8$ are taken together with the atoms to which they are attached and any intervening atoms to form a substituted or unsubstituted carbocyclyl or substituted or unsubstituted heterocyclyl, or independently an $R^7$ and $R^e$ are taken together with intervening atoms to form a substituted or unsubstituted aryl, substituted or unsubstituted heteroaryl, substituted or unsubstituted carbocyclyl, or substituted or unsubstituted heterocyclyl.

In some embodiments, each $R^8$ is independently selected from a group consisting of H, halo, $-C_{1-9}$alkyl, $-C_{2-9}$alkenyl, $-C_{2-9}$alkynyl, $-NR^9R^{10}$, $-OR^9$, $-C_{1-9}$alkyl$CO_2R^9$, $-C_{1-9}$alkyl$CO_2R^9$, $-C_{2-9}$alkenyl$CO_2R^9$, $-C_{2-9}$alkynyl$CO_2R^9$, and -carbocyclyl-$CO_2R^9$, or independently, an $R^7$ and an $R^8$ are taken together with the atoms to which they are attached to form a substituted or unsubstituted carbocyclyl or substituted or unsubstituted heterocyclyl, or independently, each $R^8$ attached to a ring atom forming part of the substituted or unsubstituted aryl or a substituted or unsubstituted heteroaryl is absent.

In some embodiments, each $R^9$ is independently selected from a group consisting of H, $C_{2-9}$alkenyl, $-C_{2-9}$alkynyl, carbocyclyl, $-C_{1-9}$alkyl$R^{11}$, $C_{2-9}$alkenyl$R^{11}$, $-C_{2-9}$alkynyl$R^{11}$, -carbocyclyl-$R^{11}$, $-C_{1-9}$alkyl$CO_2R^{12}$, $C_{2-9}$alkenyl$CO_2R^{12}$, —$C_{2-9}$alkynyl$CO_2R^{12}$, -carbocyclyl-$CO_2R^{12}$, —$C_{1-9}$alkyl-$N(R^{12})OR^{12}$, $C_{2-9}$alkenyl-$N(R^{12})OR^{12}$, —$C_{2-9}$alkynyl-$N(R^{12})OR^{12}$, -carbocyclyl-$N(R^{12})OR^{12}$, —$C_{1-9}$alkyl-$OR^{12}$, $C_{2-9}$alkenyl-$OR^{12}$, —$C_{2-9}$alkynyl-$OR^{12}$, -carbocyclyl-$OR^{12}$, substituted or unsubstituted aryl, substituted or unsubstituted heteroaryl, substituted or unsubstituted carbocyclyl, and substituted or unsubstituted heterocyclyl.

In some embodiments, each $R^{10}$ is independently selected from a group consisting of H, —$OR^9$, —CH(=NH)—, —C(=O)$OR^9$, substituted or unsubstituted aryl, substituted or unsubstituted heteroaryl, substituted or unsubstituted carbocyclyl, and substituted or unsubstituted heterocyclyl.

In some embodiments, each $R^{11}$ is independently selected from a group consisting of substituted or unsubstituted aryl, substituted or unsubstituted heteroaryl, substituted or unsubstituted carbocyclyl, and substituted or unsubstituted heterocyclyl.

In some embodiments, each $R^{12}$ is independently selected from a group consisting of H, —$(CH_2)_{0-3}$—$R_{11}$, —$C(R^{13})_2OC(O)C_{1-9}$alkyl, —$C(R^{13})_2OC(O)R^{11}$, —$C(R^{13})_2OC(O)OC_{1-9}$alkyl and —$C(R^{13})_2OC(O)OR^{11}$.

In some embodiments, each $R^{13}$ is independently selected from a group consisting of H and $C_{1-4}$alkyl.

In some embodiments, each X is independently selected from a group consisting of H, —$CO_2R^{12}$, and carboxylic acid isosteres.

In some embodiments, m is independently zero or an integer from 1 to 2.

In some embodiments, the bond represented by a dashed and solid line represents a bond selected from the group consisting of a single bond and a double bond.

In some embodiments, each $C_{1-9}$alkyl, $C_{2-9}$alkenyl, and $C_{2-9}$alkynyl is optionally substituted.

In some embodiments, formula I has the defined stereochemistry at 3-position shown in formula Ia:

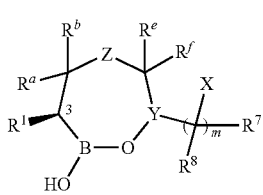

Ia

In some embodiments wherein Y is $CR^6$, formula I has the defined 3,7-trans-stereochemistry shown in formula Ib:

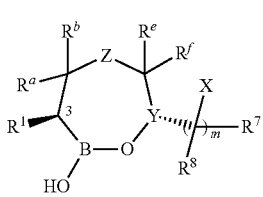

Ib

In some embodiments wherein Y is $CR^6$, formula I has the defined 3,7-cis-stereochemistry shown in formula Ic:

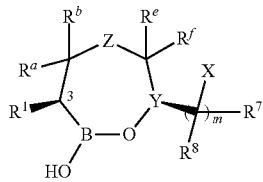

Ic

In some embodiments, $R^1$ is —NHC(=O)$R^9$.
In some embodiments, $R^9$ is —$C_{1-9}$alkyl$R^{11}$.
In some embodiments, $R^{11}$ is substituted or unsubstituted aryl or substituted or unsubstituted heteroaryl.
In some embodiments, $R^{11}$ is thien-2-yl.
In some embodiments, $R^{11}$ is —$N(R^9)C(=O)C(=NR^{10})R^9$.
In some embodiments, $R^1$ is —$N(R^9)C(=O)C(=CR^9R^{10})R^9$.
In some embodiments, $R^9$ is —$C_{1-9}$alkyl.
In some embodiments, $R^9$ is —$C_{1-9}$alkyl$R^{11}$.
In some embodiments, $R^9$ is —$C_{1-9}$alkyl$CO_2R^{12}$.
In some embodiments, $R^9$ is substituted or unsubstituted heteroaryl.
In some embodiments, $G^1$ is a bond.
In some embodiments, $G^2$ is —$C(R^eR^f)$—.
In some embodiments, $G^2$ is —C(=O)—.
In some embodiments, $G^2$ is C(=O)C($R^eR^f$)—.
In some embodiments, $G^1$ is —$C(R^aR^b)$— and $G^2$ is —$C(R^eR^f)$—.
In some embodiments, Z is O.
In some embodiments, Z is S.
In some embodiments, Z is —$N(R^9)$—.
In some embodiments, Z is —N[C(=O)$R^9$]—.
In some embodiments, Z is —N[C(=O)$OR^9$]—.
In some embodiments, Z is —$C(R^9R^{10})$—.
In some embodiments, Z is —$N(R^k)$—.
In some embodiments, Y is $CR^6$.
In some embodiments, Y is N.
In some embodiments, m is 1.
In some embodiments, $R^7$ and $R^8$ are H.
In some embodiments, $R^{10}$ is —$OR^9$—.
In some embodiments, $R^{10}$ is —C(=O)$OR^9$—.
In some embodiments, $R^{11}$ is substituted or unsubstituted aryl.
In some embodiments, $R^{11}$ is substituted or unsubstituted heteroaryl.
In some embodiments, $R^{11}$ is substituted or unsubstituted carbocyclyl.
In some embodiments, $R^{11}$ is substituted or unsubstituted heterocyclyl.
In some embodiments, X is $CO_2R^{12}$ or carboxylic acid isosteres.
In some embodiments, X is $CO_2H$.

Definitions

Terms and substituents are given their ordinary meaning unless defined otherwise, and may be defined when introduced and retain their definitions throughout unless otherwise specified, and retain their definitions whether alone or as part of another group unless otherwise specified.

As used herein, "alkyl" means a branched, or straight chain saturated chemical group containing only carbon and hydrogen, such as methyl, isopropyl, isobutyl, sec-butyl and pentyl. In various embodiments, alkyl groups can either be unsubstituted or substituted with one or more substituents, e.g., halogen, hydroxyl, substituted hydroxyl, acyloxy, amino, substituted amino, amido, cyano, nitro, guanidino, amidino, mercapto, substituted mercapto, carboxy, sulfonyloxy, carbonyl, benzyloxy, aryl, heteroaryl, carbocyclyl, heterocyclyl, or other functionality that may be suitably blocked with a protecting group. Typically, alkyl groups will comprise 1 to 20 carbon atoms, 1 to 9 carbon atoms, preferably 1 to 6, and more preferably 1 to 5 carbon atoms.

As used herein, "alkenyl" means a straight or branched chain chemical group containing only carbon and hydrogen and containing at least one carbon-carbon double bond, such as 1-propenyl, 2-propenyl, 2-methyl-1-propenyl, 1-butenyl, 2-butenyl, and the like. In various embodiments, alkenyl groups can either be unsubstituted or substituted with one or more substituents, e.g., halogen, hydroxyl, substituted hydroxyl, acyloxy, amino, substituted amino, amido, cyano, nitro, guanidino, amidino, mercapto, substituted mercapto, carboxy, sulfonyloxy, carbonyl, benzyloxy, aryl, heteroaryl, carbocyclyl, heterocyclyl, or other functionality that may be suitably blocked with a protecting group. Typically, alkenyl groups will comprise 2 to 20 carbon atoms, 2 to 9 carbon atoms, preferably 2 to 6, and more preferably 2 to 5 carbon atoms.

As used herein, "alkynyl" means a straight or branched chain chemical group containing only carbon and hydrogen and containing at least one carbon-carbon triple bond, such as 1-propynyl, 1-butynyl, 2-butynyl, and the like. In various embodiments, alkynyl groups can either be unsubstituted or substituted with one or more substituents, e.g., halogen, hydroxyl, substituted hydroxyl, acyloxy, amino, substituted amino, amido, cyano, nitro, guanidino, amidino, mercapto, substituted mercapto, carboxy, sulfonyloxy, carbonyl, benzyloxy, aryl, heteroaryl, carbocyclyl, heterocyclyl, or other functionality that may be suitably blocked with a protecting group. Typically, alkynyl groups will comprise 2 to 20 carbon atoms, 2 to 9 carbon atoms, preferably 2 to 6, and more preferably 2 to 5 carbon atoms.

As used herein, "carbocyclyl" means a non-aromatic cyclic ring system containing only carbon atoms in the ring system backbone, such as cyclopropyl, cyclobutyl, cyclopentyl, cyclohexyl, and cyclohexenyl. Carbocyclyls may include multiple fused rings. Carbocyclyls may have any degree of saturation provided that at least one ring in the ring system is not aromatic. In various embodiments, carbocyclyl groups can either be unsubstituted or substituted with one or more substituents, e.g., halogen, alkoxy, acyloxy, amino, amido, cyano, nitro, hydroxyl, mercapto, carboxy, carbonyl, benzyloxy, aryl, heteroaryl, or other functionality that may be suitably blocked with a protecting group. Typically, carbocyclyl groups will comprise 3 to 10 carbon atoms, preferably 3 to 6.

As used herein, "cycloalkyl" means a fully saturated carbocyclyl ring system. Examples include cyclopropyl, cyclobutyl, cyclopentyl, and cyclohexyl.

As used herein, "cycloalkenyl" means a carbocyclyl ring system having at least one double bond. An example is cyclohexenyl.

As used herein, "lower alkyl" means a subset of alkyl, and thus is a hydrocarbon substituent, which is linear, or branched. Preferred lower alkyls are of 1 to about 4 carbons, and may be branched or linear. Examples of lower alkyl include butyl, propyl, isopropyl, ethyl, and methyl. Likewise, radicals using the terminology "lower" refer to radicals preferably with 1 to about 4 carbons in the alkyl portion of the radical.

As used herein, "aryl" means an aromatic radical having a single-ring (e.g., phenyl) or multiple condensed rings (e.g., naphthyl or anthryl) with only carbon atoms present in the ring backbone. In various embodiments, aryl groups can either be unsubstituted or substituted with one or more substituents, e.g., amino, cyano, hydroxyl, lower alkyl, haloalkyl, alkoxy, nitro, halo, mercapto, carboxy, carbonyl, benzyloxy, aryl, heteroaryl, and other substituents. Some embodiments include substitution with an alkoxy group, which may be further substituted with one or more substituents, e.g., amino, cyano, hydroxyl, lower alkyl, haloalkyl, alkoxy, nitro, halo, mercapto, and other substituents. A preferred aryl is phenyl.

As used herein, the term "heteroaryl" means an aromatic radical having one or more heteroatom(s) (e.g., N, O, or S) in the ring backbone and may include a single ring (e.g., pyridine) or multiple condensed rings (e.g., quinoline). In various embodiments, heteroaryl groups can either be unsubstituted or substituted with one or more substituents, e.g., amino, cyano, hydroxyl, lower alkyl, haloalkyl, alkoxy, nitro, halo, mercapto, carboxy, carbonyl, benzyloxy, aryl, heteroaryl, and other substituents. Examples of heteroaryl include thienyl, pyrridyl, furyl, oxazolyl, oxadiazolyl, pyrollyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl, quinolinyl, quinazolinyl and others.

In these definitions it is contemplated that substitution on the aryl and heteroaryl rings is within the scope of certain embodiments. Where substitution occurs, the radical is called substituted aryl or substituted heteroaryl. Preferably one to three and more preferably one or two substituents occur on the aryl ring. Though many substituents will be useful, preferred substituents include those commonly found in aryl compounds, such as alkyl, cycloalkyl, hydroxy, alkoxy, cyano, halo, haloalkyl, mercapto and the like.

As used herein, "amide" or "amido" includes both RNR'CO— (in the case of R=alkyl, alkaminocarbonyl-) and RCONR'—(in the case of R=alkyl, alkyl carbonylamino-). "Amide" or "amido" includes a H—CON—, alkyl-CON—, carbocyclyl-CON—, aryl-CON—, heteroaryl-CON— or heterocyclyl-CON— group, wherein the alkyl, carbocyclyl, aryl or heterocyclyl group is as herein described.

As used herein, the term "ester" includes both ROCO— (in the case of R=alkyl, alkoxycarbonyl-) and RCOO— (in the case of R=alkyl, alkylcarbonyloxy-).

As used herein, "acyl" means an H—CO—, alkyl-CO—, carbocyclyl-CO—, aryl-CO—, heteroaryl-CO— or heterocyclyl-CO— group wherein the alkyl, carbocyclyl, aryl or heterocyclyl group is as herein described. Preferred acyls contain a lower alkyl. Exemplary alkyl acyl groups include formyl, acetyl, propanoyl, 2-methylpropanoyl, t-butylacetyl, butanoyl and palmitoyl.

As used herein, "halo or halide" is a chloro, bromo, fluoro or iodo atom radical. Chloro and fluoro are preferred halides. The term "halo" also contemplates terms sometimes referred to as "halogen", or "halide".

As used herein, "heterocyclyl" means a non-aromatic cyclic ring system comprising at least one heteroatom in the ring system backbone. Heterocyclyls may include multiple fused rings. Heterocyclyls may have any degree of saturation provided that at least one ring in the ring system is not aromatic. The heteroatom(s) may be present in either a non-aromatic or aromatic ring in the ring system. In various embodiments, heterocyclyls may be substituted or unsubstituted with one or more substituents, e.g., halogen, alkoxy, acyloxy, amino, amido, cyano, nitro, hydroxyl, mercapto, carboxy, carbonyl, benzyloxy, aryl, heteroaryl, and other substituents, and are attached to other groups via any available valence, preferably any available carbon or nitrogen. Preferred heterocycles are of 5-7 members. In six membered monocyclic heterocycles, the heteroatom(s) are selected from one up to three of O, N or S, and when the heterocycle is five membered, preferably it has one or two heteroatoms selected from O, N, or S. Examples of heterocyclyl include pyrrolidinyl, piperidinyl, azepanyl, tetrahydrofuranyl, tetrahydropyranyl, oxepanyl, tetrahydrothiophenyl, tetrahydrothiopyranyl, thiepanyl, indolinyl and dihydrobenzofuranyl.

As used herein, "substituted amino" means an amino radical which is substituted by one or two alkyl, cycloalkyl, aryl, heteroaryl or heterocyclyl groups, wherein the alkyl, aryl, heteroaryl, cycloalkyl or heterocyclyl are defined as above.

As used herein, "substituted hydroxyl" means RO— group wherein R is an alkyl, an aryl, heteroaryl, cycloalkyl or a heterocyclyl group, wherein the alkyl, cycloalkyl, aryl, heteroaryl or heterocyclyl are defined as above.

As used herein, "substituted thiol" means RS— group wherein R is an alkyl, an aryl, heteroaryl, cycloalkyl or a heterocyclyl group, wherein the alkyl, cycloalkyl, aryl, heteroaryl or heterocyclyl are defined as above.

As used herein, "sulfonyl" means an alkyl$SO_2$, aryl$SO_2$, heteroaryl$SO_2$, carbocyclyl$SO_2$, or heterocyclyl-$SO_2$ group wherein the alkyl, carbocyclyl, aryl, heteroaryl or heterocyclyl are defined as above.

As used herein, "sulfamido" means an alkyl-N—S(O)$_2$N—, aryl-NS(O)$_2$N—, heteroaryl-NS(O)$_2$N—, carbocyclyl-NS(O)$_2$N or heterocyclyl-NS(O)$_2$N— group wherein the alkyl, carbocyclyl, aryl, heteroaryl or heterocyclyl group is as herein described.

As used herein, "sulfonamido" means an alkyl-S(O)$_2$N—, aryl-S(O)$_2$N—, heteroaryl-S(O)$_2$N—, carbocyclyl-S(O)$_2$N— or heterocyclyl-S(O)$_2$N— group wherein the alkyl, carbocyclyl, aryl, heteroaryl or heterocyclyl group is as herein described.

As used herein, "ureido" means an alkyl-NCON—, aryl-NCON—, heteroaryl-NCON—, carbocyclyl-NCON—, heterocyclyl-NCON— group or heterocyclyl-CON— group wherein the heterocyclyl group is attached by a ring nitrogen, and wherein the alkyl, carbocyclyl, aryl, heteroaryl or heterocyclyl group is as herein described.

As used herein, "guanidino" means an alkyl-NC(=NR')N—, aryl-NC(=NR')N—, heteroaryl-NC(=NR')N—, carbocyclyl-NC(=NR')N— or heterocyclyl-NC(=NR')N— group wherein R' is an H, substituted or unsubstituted hydroxyl, CN, alkyl, aryl, heteroaryl or a heterocyclyl group, wherein the alkyl, carbocyclyl, aryl, heteroaryl or heterocyclyl group is as herein described.

As used herein, a substituted group is derived from the unsubstituted parent group in which there has been an exchange of one or more hydrogen atoms for another atom or group. When substituted, the substituent group(s) is (are) substituted with one or more substituent(s) individually and independently selected from $C_1$-$C_6$ alkyl, $C_1$-$C_6$ alkenyl, $C_1$-$C_6$ alkynyl, $C_3$-$C_7$ carbocyclyl (optionally substituted with halo, alkyl, alkoxy, carboxyl, haloalkyl, CN, $SO_2$-alkyl, $CF_3$, and $OCF_3$), $C_1$-$C_6$ heteroalkyl, 5-7 membered heterocyclyl (e.g., tetrahydrofuryl) (optionally substituted with halo, alkyl, alkoxy, carboxyl, CN, $SO_2$-alkyl, $CF_3$, and $OCF_3$), aryl (optionally substituted with halo, alkyl, aryl optionally substituted with $C_1$-$C_6$ alkyl, arylalkyl, alkoxy, carboxyl, CN, $SO_2$-alkyl, $CF_3$, and $OCF_3$), arylalkyl (optionally substituted with halo, alkyl, alkoxy, aryl, carboxyl, CN, $SO_2$-alkyl, $CF_3$, and $OCF_3$), heteroaryl (optionally substituted with halo, alkyl, alkoxy, aryl, aralkyl, carboxyl, CN, $SO_2$-alkyl, $CF_3$, and $OCF_3$), heteroarylalkyl (optionally substituted with halo, alkyl, alkoxy, aryl, carboxyl, CN, $SO_2$-alkyl, $CF_3$, and $OCF_3$), halo (e.g., chloro, bromo, iodo and fluoro), cyano, hydroxy, $C_1$-$C_6$ alkoxy, $C_1$-$C_6$ alkoxyalkyl (i.e., ether), aryloxy, sulfhydryl (mercapto), halo($C_1$-$C_6$)alkyl (e.g., $CF_3$), $C_1$-$C_6$ alkylthio, arylthio, amino (—$NH_2$), mono- and di-($C_1$-$C_6$)alkyl amino, quaternary ammonium salts, amino($C_1$-$C_6$)alkoxy (e.g., —O($CH_2$)$_4NH_2$), amino($C_1$-$C_6$)alkoxyalkyl (e.g., —$CH_2$—O—($CH_2$)$_2NH_2$), hydroxy($C_1$-$C_6$)alkyl amino, amino($C_1$-$C_6$)alkylthio (e.g., —S($CH_2$)$_2NH_2$), cyanoamino, nitro, carbamyl, oxo (=O), carboxy, glycolyl, glycyl, hydrazino, guanidinyl, sulfamyl, sulfonyl, sulfinyl, thiocarbonyl, thiocarboxy, C-amide, N-amide, N-carbamate, O-carbamate, and urea. Wherever a group is described as "optionally substituted" that group can be substituted with the above substituents.

In some embodiments, substituted group(s) is (are) substituted with one or more substituent(s) individually and independently selected from $C_1$-$C_6$ alkyl, $C_3$-$C_7$ carbocycle, amino (—$NH_2$), amino($C_1$-$C_6$)alkoxy, carboxyl, oxo (=O), $C_1$-$C_6$ alkylthio, amino($C_1$-$C_6$)alkylthio, guanidinyl, aryl, 5-7 membered heterocyclyl, heteroarylalkyl, hydroxy, halo, amino($C_1$-$C_6$)alkoxy, and amino($C_1$-$C_6$)alkoxyalkyl.

In some embodiments, substituted group(s) is (are) substituted with one or more substituent(s) individually and independently selected from $C_1$-$C_6$ alkyl, amino (—$NH_2$), amino($C_1$-$C_6$)alkoxy, carboxyl, oxo (=O), $C_1$-$C_6$ alkylthio, amino($C_1$-$C_6$)alkylthio, guanidinyl, hydroxy, halo, amino($C_1$-$C_6$) alkoxy, and amino($C_1$-$C_6$)alkoxyalkyl.

In some embodiments, substituted group(s) is (are) substituted with one or more substituent(s) individually and independently selected from $C_1$-$C_6$ alkyl, amino (—$NH_2$), carboxyl, oxo (=O), guanidinyl, hydroxy, and halo.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —$CH_2$—, —$CH_2CH_2$—, —$CH_2CH(CH_3)CH_2$—, and the like. Other radical naming conventions clearly indicate that the radical is a di-radical. For example, as used herein, "alkylene" means a branched, or straight chain saturated di-radical chemical group containing only carbon and hydrogen, such as methylene, isopropylene, isobutylene, sec-butylene, and pentylene, that is attached to the rest of the molecule via two points of attachment. As used herein, "alkenylene" means a straight or branched chain di-radical chemical group containing only carbon and hydrogen and containing at least one carbon-carbon double bond, such as 1-propenylene, 2-propenylene, 2-methyl-1-propenylene, 1-butenylene, and 2-butenylene, that is attached to the rest of the molecule via two points of attachment.

As used herein, "isosteres" of a chemical group are other chemical groups that exhibit the same or similar properties. For example, tetrazole is an isostere of carboxylic acid because it mimics the properties of carboxylic acid even though they both have very different molecular formulae. Tetrazole is one of many possible isosteric replacements for carboxylic acid. Other carboxylic acid isosteres contemplated include —$SO_3H$, —$SO_2HNR^9$, —$PO_2(R^9)_2$, —$PO_3(R^9)_2$, —$CONHNSO_2R^9$, —$COHNSO_2R^9$, and $CONR^9CN$, where $R^9$ is as defined above. In addition, carboxylic acid isosteres can include 5-7 membered carbocycles or heterocycles containing any combination of $CH_2$, O, S, or N in any chemically stable oxidation state, where any of the atoms of said ring structure are optionally substituted in one or more positions. The following structures are non-limiting examples of carbocyclic and heterocyclic isosteres contemplated. The atoms of said ring structure may be optionally substituted at one or more positions with $R^9$ as defined above.

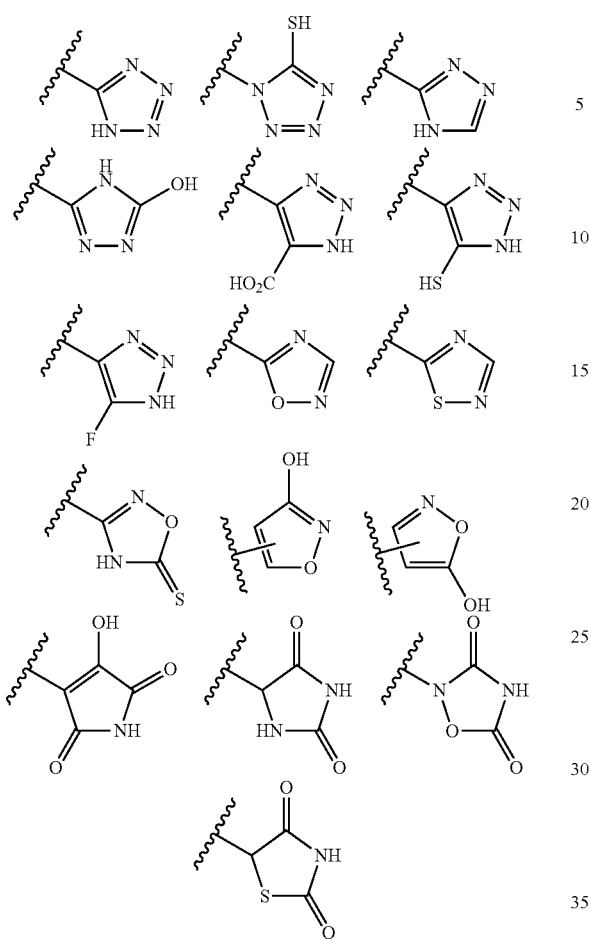

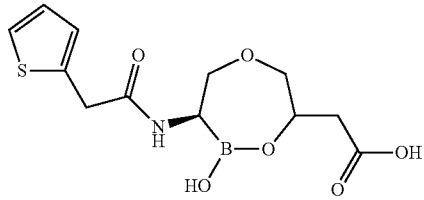

example, Compound 1 may exist in combination with one or more open-chain form (1a), bicyclic form (1b) dimeric form (1c), cyclic dimeric form (1d), trimeric form (1e), cyclic trimeric form (1f), and the like.

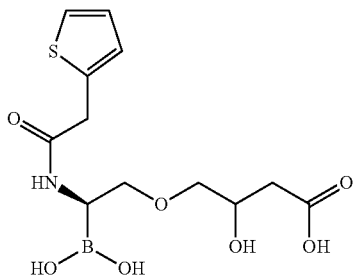

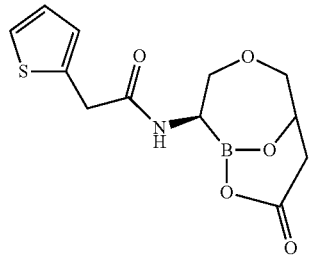

It is also contemplated that when chemical substituents are added to a carboxylic isostere, the compound retains the properties of a carboxylic isostere. It is contemplated that when a carboxylic isostere is optionally substituted with one or more moieties selected from $R^9$ as defined above, then the substitution and substitution position is selected such that it does not eliminate the carboxylic acid isosteric properties of the compound. Similarly, it is also contemplated that the placement of one or more $R^9$ substituents upon a carbocyclic or heterocyclic carboxylic acid isostere is not a substitution at one or more atom(s) that maintain(s) or is/are integral to the carboxylic acid isosteric properties of the compound, if such substituent(s) would destroy the carboxylic acid isosteric properties of the compound.

Other carboxylic acid isosteres not specifically exemplified in this specification are also contemplated.

The skilled artisan will recognize that some structures described herein may be resonance forms or tautomers of compounds that may be fairly represented by other chemical structures, even when kinetically; the artisan recognizes that such structures are only a very small portion of a sample of such compound(s). Such compounds are considered within the scope of the structures depicted, though such resonance forms or tautomers are not represented herein.

In some embodiments, due to the facile exchange of boron esters, the compounds described herein may convert to or exist in equilibrium with alternate forms. Accordingly, in some embodiments, the compounds described herein may exist in combination with one or more of these forms. For

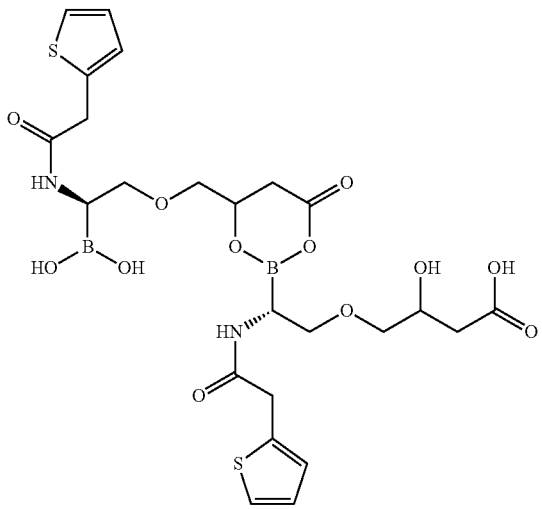

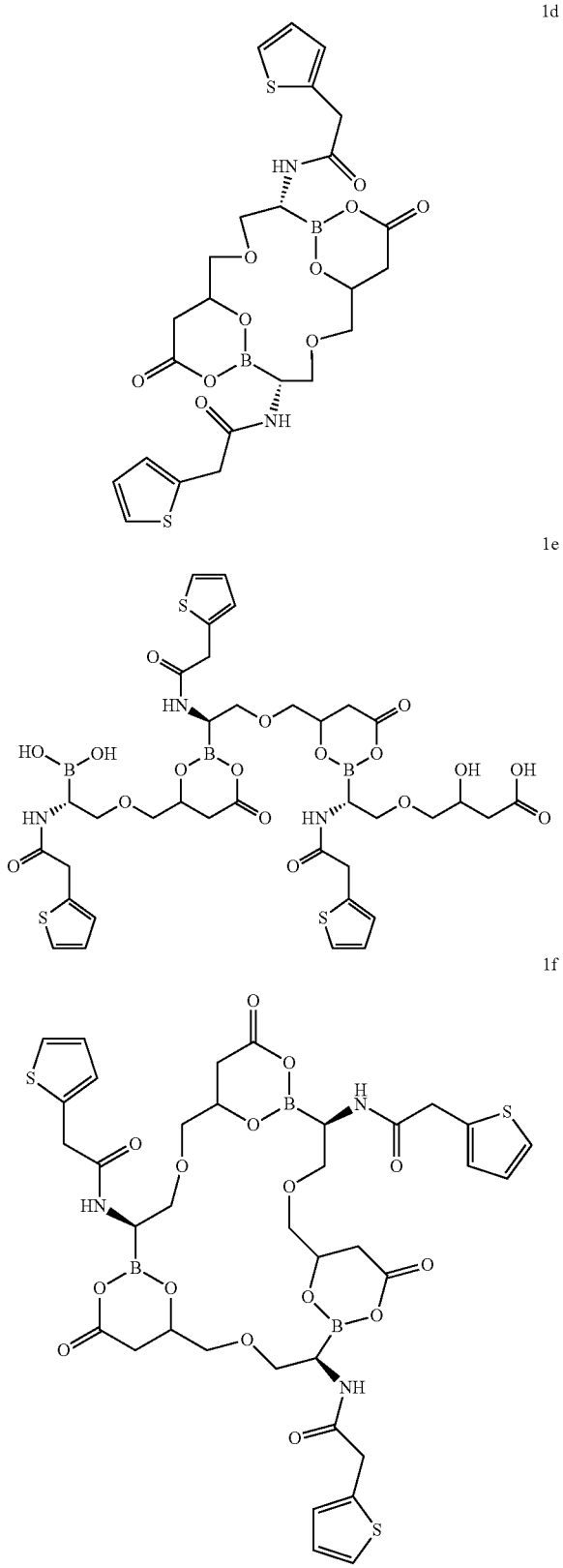 [SMILES: O=C(Cc1cccs1)N[C@H]1COCC2CC(=O)OB(O2)[C@@H](NC(=O)Cc2cccs2)COCC2CC(=O)OB1O2 ; O=C(O)CC(O)COC[C@H](NC(=O)Cc1cccs1)B1OC(=O)CC(COC[C@H](NC(=O)Cc2cccs2)B2OC(=O)CC(COC[C@H](NC(=O)Cc3cccs3)B(O)O)O2)O1 ; O=C(Cc1cccs1)N[C@H]1COCC2CC(=O)OB(O2)[C@@H](NC(=O)Cc2cccs2)COCC2CC(=O)OB(O2)[C@@H](NC(=O)Cc2cccs2)COCC2CC(=O)OB1O2]

The compounds provided herein may encompass various stereochemical forms. The compounds also encompasses diastereomers as well as optical isomers, e.g. mixtures of enantiomers including racemic mixtures, as well as individual enantiomers and diastereomers, which arise as a consequence of structural asymmetry in certain compounds. Separation of the individual isomers or selective synthesis of the individual isomers is accomplished by application of various methods which are well known to practitioners in the art.

The term "agent" or "test agent" includes any substance, molecule, element, compound, entity, or a combination thereof. It includes, but is not limited to, e.g., protein, polypeptide, peptide or mimetic, small organic molecule, polysaccharide, polynucleotide, and the like. It can be a natural product, a synthetic compound, or a chemical compound, or a combination of two or more substances. Unless otherwise specified, the terms "agent", "substance", and "compound" are used interchangeably herein.

The term "analog" is used herein to refer to a molecule that structurally resembles a reference molecule but which has been modified in a targeted and controlled manner, by replacing a specific substituent of the reference molecule with an alternate substituent. Compared to the reference molecule, an analog would be expected, by one skilled in the art, to exhibit the same, similar, or improved utility. Synthesis and screening of analogs, to identify variants of known compounds having improved characteristics (such as higher binding affinity for a target molecule) is an approach that is well known in pharmaceutical chemistry.

The term "mammal" is used in its usual biological sense. Thus, it specifically includes humans, cattle, horses, dogs, cats, rats and mice but also includes many other species.

The term "microbial infection" refers to the invasion of the host organism, whether the organism is a vertebrate, invertebrate, fish, plant, bird, or mammal, by pathogenic microbes. This includes the excessive growth of microbes that are normally present in or on the body of a mammal or other organism. More generally, a microbial infection can be any situation in which the presence of a microbial population(s) is damaging to a host mammal. Thus, a mammal is "suffering" from a microbial infection when excessive numbers of a microbial population are present in or on a mammal's body, or when the effects of the presence of a microbial population(s) is damaging the cells or other tissue of a mammal. Specifically, this description applies to a bacterial infection. Note that the compounds of preferred embodiments are also useful in treating microbial growth or contamination of cell cultures or other media, or inanimate surfaces or objects, and nothing herein should limit the preferred embodiments only to treatment of higher organisms, except when explicitly so specified in the claims.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press.

The term "pharmaceutically acceptable salt" refers to salts that retain the biological effectiveness and properties of the compounds of the preferred embodiments and, which are not biologically or otherwise undesirable. In many cases, the compounds of the preferred embodiments are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

"Solvate" refers to the compound formed by the interaction of a solvent and an EPI, a metabolite, or salt thereof. Suitable solvates are pharmaceutically acceptable solvates including hydrates.

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

A therapeutic effect relieves, to some extent, one or more of the symptoms of the infection, and includes curing an infection. "Curing" means that the symptoms of active infection are eliminated, including the elimination of excessive members of viable microbe of those involved in the infection. However, certain long-term or permanent effects of the infection may exist even after a cure is obtained (such as extensive tissue damage).

"Treat," "treatment," or "treating," as used herein refers to administering a pharmaceutical composition for prophylactic and/or therapeutic purposes. The term "prophylactic treatment" refers to treating a patient who is not yet infected, but who is susceptible to, or otherwise at risk of, a particular infection, whereby the treatment reduces the likelihood that the patient will develop an infection. The term "therapeutic treatment" refers to administering treatment to a patient already suffering from an infection.

Administration and Pharmaceutical Compositions

Some embodiments include pharmaceutical compositions comprising: (a) a safe and therapeutically effective amount of the cyclic boronic acid ester derivative, or its corresponding enantiomer, diastereoisomer or tautomer, or pharmaceutically acceptable salt; and (b) a pharmaceutically acceptable carrier.

The cyclic boronic acid ester derivatives are administered at a therapeutically effective dosage, e.g., a dosage sufficient to provide treatment for the disease states previously described. While human dosage levels have yet to be optimized for the compounds of the preferred embodiments, generally, a daily dose for most of the cyclic boronic acid ester derivatives described herein is from about 0.25 mg/kg to about 120 mg/kg or more of body weight, from about 0.5 mg/kg or less to about 70 mg/kg, from about 1.0 mg/kg to about 50 mg/kg of body weight, or from about 1.5 mg/kg to about 10 mg/kg of body weight. Thus, for administration to a 70 kg person, the dosage range would be from about 17 mg per day to about 8000 mg per day, from about 35 mg per day or less to about 7000 mg per day or more, from about 70 mg per day to about 6000 mg per day, from about 100 mg per day to about 5000 mg per day, or from about 200 mg to about 3000 mg per day. The amount of active compound administered will, of course, be dependent on the subject and disease state being treated, the severity of the affliction, the manner and schedule of administration and the judgment of the prescribing physician.

Administration of the compounds disclosed herein or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarilly, vaginally, rectally, or intraocularly. Oral and parenteral administrations are customary in treating the indications that are the subject of the preferred embodiments.

The compounds useful as described above can be formulated into pharmaceutical compositions for use in treatment of these conditions. Standard pharmaceutical formulation techniques are used, such as those disclosed in Remington's The Science and Practice of Pharmacy, 21st Ed., Lippincott Williams & Wilkins (2005), incorporated by reference in its entirety.

In addition to the selected compound useful as described above, come embodiments include compositions containing a pharmaceutically-acceptable carrier. The term "pharmaceutically-acceptable carrier", as used herein, means one or more compatible solid or liquid filler diluents or encapsulating substances, which are suitable for administration to a mammal. The term "compatible", as used herein, means that the components of the composition are capable of being commingled with the subject compound, and with each other, in a manner such that there is no interaction, which would substantially reduce the pharmaceutical efficacy of the composition under ordinary use situations. Pharmaceutically-acceptable carriers must, of course, be of sufficiently high purity and sufficiently low toxicity to render them suitable for administration preferably to an animal, preferably mammal being treated.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

The compositions described herein are preferably provided in unit dosage form. As used herein, a "unit dosage form" is a composition containing an amount of a compound that is suitable for administration to an animal, preferably mammal subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, though a single administration is not specifically excluded. The skilled artisan will recognize that the formulation does not specifically contemplate the entire course of therapy and such decisions are left for those skilled in the art of treatment rather than formulation.

The compositions useful as described above may be in any of a variety of suitable forms for a variety of routes for administration, for example, for oral, nasal, rectal, topical (including transdermal), ocular, intracerebral, intracranial, intrathecal, intra-arterial, intravenous, intramuscular, or other parental routes of administration. The skilled artisan will appreciate that oral and nasal compositions comprise compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropies, surface-active agents, and encapsulating substances. Optional pharmaceutically-active materials may be included, which do not substantially interfere with the inhibitory activity of the compound. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules, granules and bulk powders. These oral forms comprise a safe and effective amount, usually at least about 5%, with a maximum of about 90%, of the compound. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions described herein may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PI-IMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

In a similar vein, an ophthalmically acceptable antioxidant includes, but is not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium, although other chelating agents may also be used in place or in conjunction with it.

For topical use, creams, ointments, gels, solutions or suspensions, etc., containing the compound disclosed herein are employed. Topical formulations may generally be comprised of a pharmaceutical carrier, co-solvent, emulsifier, penetration enhancer, preservative system, and emollient.

For intravenous administration, the compounds and compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, *PDA JPharm Sci and Tech* 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The compositions for intravenous administration may be provided to caregivers in the form of one more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

The actual dose of the active compounds described herein depends on the specific compound, and on the condition to be treated; the selection of the appropriate dose is well within the knowledge of the skilled artisan.

Methods of Treatment

Some embodiments of the present invention include methods of treating bacterial infections with the compounds and compositions comprising cyclic boronate ester derivatives described herein. Some methods include administering a compound, composition, pharmaceutical composition described herein to a subject in need thereof. In some embodiments, a subject can be an animal, e.g., a mammal, a human. In some embodiments, the bacterial infection comprises a bacteria described herein. As will be appreciated from the foregoing, methods of treating a bacterial infection include methods for preventing bacterial infection in a subject at risk thereof.

In some embodiments, the subject is a human.

Further embodiments include administering a combination of compounds to a subject in need thereof. A combination can include a compound, composition, pharmaceutical composition described herein with an additional medicament.

Some embodiments include co-administering a compound, composition, and/or pharmaceutical composition described herein, with an additional medicament. By "co-administration," it is meant that the two or more agents may be found in the patient's bloodstream at the same time, regardless of when or how they are actually administered. In one embodiment, the agents are administered simultaneously. In one such embodiment, administration in combination is accomplished by combining the agents in a single dosage form. In another embodiment, the agents are administered sequentially. In one embodiment the agents are administered through the same route, such as orally. In another embodiment, the agents are administered through different routes, such as one being administered orally and another being administered i.v.

Examples of additional medicaments include an antibacterial agent, antifungal agent, an antiviral agent, an anti-inflammatory agent and an anti-allergic agent.

Preferred embodiments include combinations of a compound, composition or pharmaceutical composition described herein with an antibacterial agent such as a β-lactam. Examples of such β-lactams include Amoxicillin, Ampicillin (e.g., Pivampicillin, Hetacillin, Bacampicillin, Metampicillin, Talampicillin), Epicillin, Carbenicillin (Carindacillin), Ticarcillin, Temocillin, Azlocillin, Piperacillin, Mezlocillin, Mecillinam (Pivmecillinam), Sulbenicillin, Benzylpenicillin (G), Clometocillin, Benzathine benzylpenicillin, Procaine benzylpenicillin, Azidocillin, Penamecillin, Phenoxymethylpenicillin (V), Propicillin, Benzathine phenoxymethylpenicillin, Pheneticillin, Cloxacillin (e.g., Dicloxacillin, Flucloxacillin), Oxacillin, Methicillin, Nafcillin, Faropenem, Biapenem, Doripenem, Ertapenem, Imipenem, Meropenem, Panipenem, Cefazolin, Cefacetrile, Cefadroxil, Cefalexin, Cefaloglycin, Cefalonium, Cefaloridine, Cefalotin, Cefapirin, Cefatrizine, Cefazedone, Cefazaflur, Cefradine, Cefroxadine, Ceftezole, Cefaclor, Cefamandole, Cefminox, Cefonicid, Ceforanide, Cefotiam, Cefprozil, Cefbuperazone, Cefuroxime, Cefuzonam, Cefoxitin, Cefotetan, Cefinetazole, Loracarbef, Cefixime, Ceftazidime, Ceftriaxone, Cefcapene, Cefdaloxime, Cefdinir, Cefditoren, Cefetamet, Cefinenoxime, Cefodizime, Cefoperazone, Cefotaxime, Cefpimizole, Cefpiramide, Cefpodoxime, Cefsulodin, Cefteram, Ceftibuten, Ceftiolene, Ceftizoxime, Flomoxef, Latamoxef, Cefepime, Cefozopran, Cefpirome, Cefquinome, Ceftobiprole, Ceftaroline, Ceftiofur, Cefquinome, Cefovecin, Aztreonam, Tigemonam and Carumonam.

Preferred embodiments include β-lactams such as Ceftazidime, Biapenem, Doripenem, Ertapenem, Imipenem, Meropenem and Panipenem.

Additional preferred embodiments include β-lactams such as Aztreonam, Tigemonam, and Carumonam.

Some embodiments include a combination of the compounds, compositions and/or pharmaceutical compositions described herein with an additional agent, wherein the additional agent comprises a monobactam. Examples of monobactams include aztreonam, tigemonam, nocardicin A, carumonam, and tabtoxin. In some such embodiments, the compound, composition and/or pharmaceutical composition comprises a class A, C, or D β-lactamase inhibitor. Some embodiments include co-administering the compound, composition or pharmaceutical composition described herein with one or more additional agents.

Some embodiments include a combination of the compounds, compositions and/or pharmaceutical compositions described herein with an additional agent, wherein the additional agent comprises a class B β-lactamase inhibitor. An example of a class B β-lactamase inhibitor includes ME1071 (Yoshikazu Ishii et al, "In Vitro Potentiation of Carbapenems with ME1071, a Novel Metallo-β-Lactamase Inhibitor, against Metallo-β-lactamase Producing *Pseudomonas aeruginosa* Clinical Isolates." Antimicrob. Agents Chemother. doi:10.1128/AAC.01397-09 (July 2010)). Some embodiments include co-administering the compound, composition or pharmaceutical composition described herein with one or more additional agents.

Some embodiments include a combination of the compounds, compositions and/or pharmaceutical compositions described herein with an additional agent, wherein the additional agent comprises one or more agents that include a class A, B, C, or D β-lactamase inhibitor. Some embodiments include co-administering the compound, composition or pharmaceutical composition described herein with the one or more additional agents.

Indications

The compounds and compositions comprising cyclic boronate derivatives described herein can be used to treat bacterial infections. Bacterial infections that can be treated with the compounds, compositions and methods described herein can comprise a wide spectrum of bacteria. Example organisms include gram-positive bacteria, gram-negative bacteria, aerobic and anaerobic bacteria, such as *Staphylococcus, Lactobacillus, Streptococcus, Sarcina, Escherichia, Enterobacter, Klebsiella, Pseudomonas, Acinetobacter, Mycobacterium, Proteus, Campylobacter, Citrobacter, Nisseria, Baccillus, Bacteroides, Peptococcus, Clostridium, Salmonella, Shigella, Serratia, Haemophilus, Brucella* and other organisms.

More examples of bacterial infections include *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis,* or *Staphylococcus saccharolyticus.*

The following examples will further describe the present invention, and are used for the purposes of illustration only, and should not be considered as limiting.

EXAMPLES

General Procedures

Materials used in preparing the cyclic boronates described herein may be made by known methods or are commercially available. It will be apparent to the skilled artisan that methods for preparing precursors and functionality related to the compounds claimed herein are generally described in the literature including, for example, procedures described in U.S. Pat. No. 7,271,186, WO2009064414 and WO2012021455 each of which is incorporated by reference in its entirety. In these reactions, it is also possible to make use of variants which are themselves known to those of ordinary skill in this art, but are not mentioned in greater detail. The skilled artisan given the literature and this disclosure is well equipped to prepare any of the compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as March Advanced Organic Chemistry (Wiley), Carey and Sundberg, Advanced Organic Chemistry (incorporated herein by reference in its entirety) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts Protecting Groups in Organic Synthesis, 4th Ed., John Wiley & Sons (2007), incorporated herein by reference in its entirety.

The following example schemes are provided for the guidance of the reader, and represent preferred methods for making the compounds exemplified herein. These methods are not limiting, and it will be apparent that other routes may be employed to prepare these compounds. Such methods specifically include solid phase based chemistries, including combinatorial chemistry. The skilled artisan is thoroughly equipped to prepare these compounds by those methods given the literature and this disclosure. The compound numberings used in the synthetic schemes depicted below are meant for those specific schemes only, and should not be construed as or confused with same numberings in other sections of the application.

Trademarks used herein are examples only and reflect illustrative materials used at the time of the invention. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the invention.

($^1$H) nuclear magnetic resonance spectra (NMR) were measured in the indicated solvents on either a Bruker NMR spectrometer (Avance™ DRX500, 500 MHz for 1H) or Varian NMR spectrometer (Mercury 400BB, 400 MHz for 1H). Peak positions are expressed in parts per million (ppm) downfield from tetramethylsilane. The peak multiplicities are denoted as follows, s, singlet; d, doublet; t, triplet; q, quartet; quin, quintet; sex, sextet; sep, septet; non, nonet; dd, doublet of doublets; td, triplet of doublets; m, multiplet.

The following abbreviations have the indicated meanings:
Ac$_2$O=acetic anhydride
n-BuLi=n-butyllithium
t-Bu=tert-butyl
DCE=dichloroethane
DCM=dichloromethane
DIPEA=diisopropylethylamine
DMAP=4-dimethylaminopyridine
EDCI=1-ethyl-3-(3-dimethylaminopropyl)carbodiimide
ESBL=extended-spectrum β-lactamase
ESIMS=electron spray mass spectrometry
EtOAc=ethyl acetate
HOBt=hydroxybenzotriazole
LiHMDS=lithium bis(trimethylsilyl)amide
MeCN=acetonitrile
MgSO$_4$=magnesium sulfate
NaBH(OAc)$_3$=sodium triacetoxyborohydride
NaHCO$_3$=sodium bicarbonate
Na$_2$SO$_4$=sodium sulfate
NMM=N-methylmorpholine
NMR=nuclear magnetic resonance
Pd/C=palladium on carbon
TBS=tert-butyldimethylsilyl
TBSOTf=t-butyldimethylsilyl trifluoromethansulfonate
TFA=trifluoroacetic acid
THF=tetrahydrofuran
TLC=thin layer chromatography
TMS=trimethylsilyl The following example schemes are provided for the guidance of the reader, and collectively represent an example method for making the compounds provided herein. Furthermore, other methods for preparing compounds described herein will be readily apparent to the person of ordinary skill in the art in light of the following reaction schemes and examples. Unless otherwise indicated, all variables are as defined above.

Compounds of Formula I where R$^1$ is an acylamino group, Z is —O— or —S— and X is a carboxylic acid can be prepared as depicted in Scheme 1.

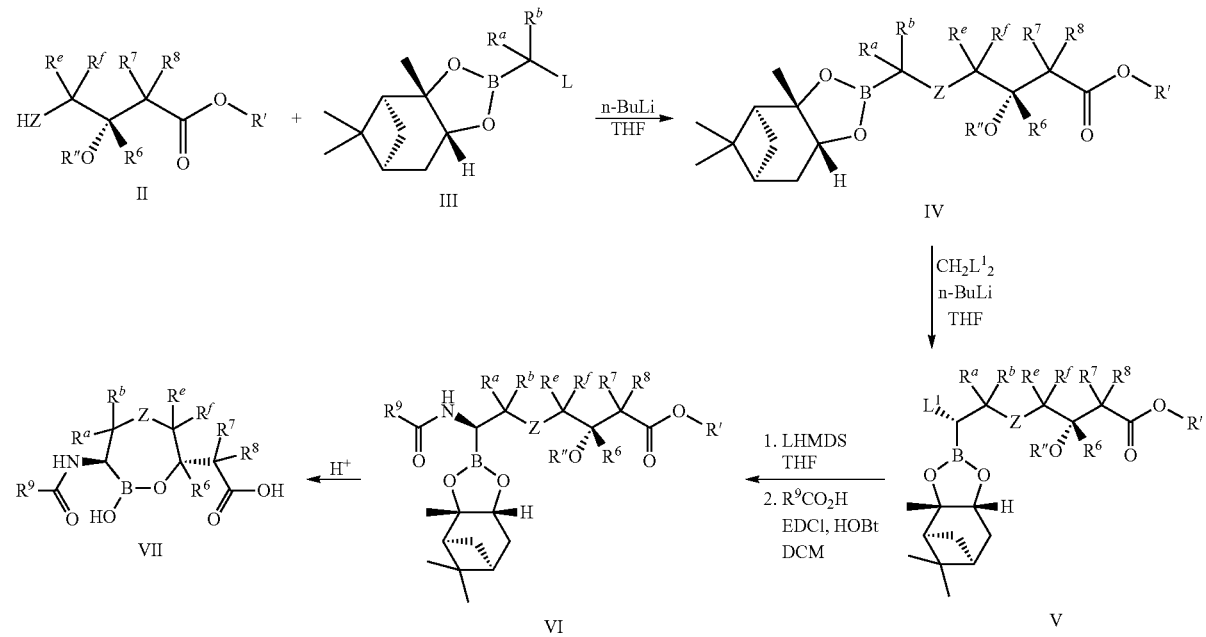

Scheme 1

Compounds of structure IV where Z is —O— can be made via lithium alkoxide formation of alcohol II (Z═—O—) [*J. Org. Chem.* (2010), 75, 3953-3957; WO0587700] and reaction with halomethyleneboronate esters [*Tetrahedron* (2005), 61, 4427-4436; *J. Am. Chem. Soc.* (1990), 112, 3964-3969]. Compounds where Z is —S— in IV may be attained via thiol version of II (Z═—S—). Such thiol compounds can be made from the corresponding alcohol by variety of known procedures (*Tetrahedron: Asymmetry* (1993), 4, 361-8). Homologation of IV to V where $L^1$ is chloro is achieved via Matteson reaction conditions with good stereocontrol [WO0946098; *Tetrahedron* (1998), 54, 10555-10607]. The chloro derivative of V can be utilized to introduce a substituted amine group at the alpha-position of boronate. Stereospecific substitution with hexamethyldisilazane gives the corresponding bis(trimethylsilyl) amide which may be reacted in situ with an acid chloride to result directly in analogs of structure VI. Such analogs of VI can also be made via coupling of the bis-TMS amine with commercially available carboxylic acids under typical amide coupling conditions (e.g., carbodiimide or HATU coupling). Simultaneous deprotection of the pinane ester, acid sensitive OR' and OR" groups and concomitant cyclization are achieved by heating with dilute HCl, affording the desired cyclic boronate derivatives of structure VII. This transformation may also be achieved by treatment with $BCl_3$ or $BBr_3$ (WO09064414). Alternatively, the deprotection may be attained via trans-esterification with isobutyl boronic acid in presence of dilute HCl (WO09064413) or via other known methods [*J. Org. Chem.* (2010), 75, 468-471].

Compounds of structure IX where $R^1$ of Formula I is an alkyl, aralkyl or aminoaryl group may be made from intermediate V as shown in Scheme 2.

Scheme 2

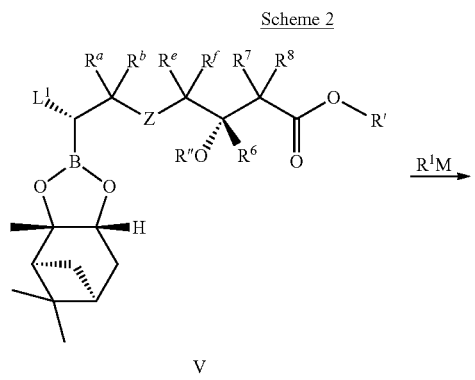

Compounds of structure IX may be made from intermediate V, where $L^1$ preferably an iodo, or bromo group [*J. Organomet. Chem.* (1992), 431, 255-70]. Such bromo derivatives may be made as analogously to the chloro compounds of Scheme 1, utilizing dibromomethane [*J. Am. Chem. Soc.* (1990), 112, 3964-969]. Displacement of the bromo group in V can be achieved by α-alkoxy substituted alkyllithium agents [*J. Am. Chem. Soc.* (1989), 111, 4399-402; *J. Am. Chem. Soc.* (1988), 110, 842-53] or organomagnesium reagents (WO0946098) or by the sodium salt of alkyl or aryl carbamate derivatives [*J. Org. Chem.* (1996), 61, 7951-54], resulting in VIII. Deprotection and cyclization of VIII to afford IX may be achieved under the conditions described in Scheme 1.

Compounds of Formula I where $R^1$ is an acylamino group, Z is —N[C(═O)$R^9$]— and X is a carboxylic acid can be prepared as depicted in Scheme 3.

Scheme 3

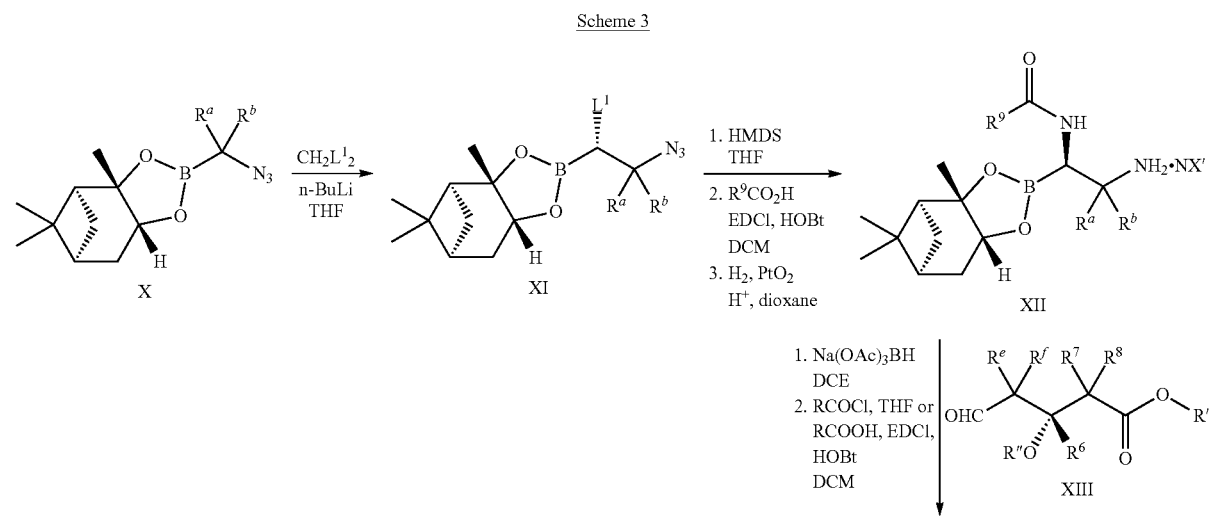

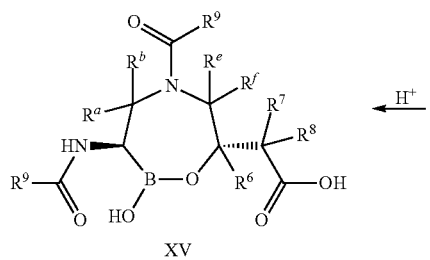

XV

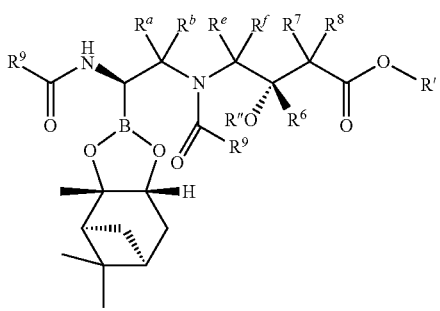

XIV

Enantiomerically pure 1,2-diamino-propyl boronate derivatives of structure XII are made utilizing Matteson protocol as described above, starting from azido-methylene boronate of structure X [*Organometallics* (1996), 15, 152-163] via halomethylene insertion product XI [*J. Organomet. Chem*. (2008), 693, 2258-2262]. Compounds of structure XII can be further transformed to XIV by well known reductive amination transformation [*J. Org. Chem*. (1996), 61, 3849-3862] with carbonyl intermediates such as XIII, followed by installation of $R^9CO$— group on the resulting amine. Cyclic boronates of structure XV are attained from intermediate XIV by simultaneous deprotection and cyclization in acid hydrolysis conditions described in Scheme 1. A sequential deprotection and cyclization protocol may be followed where OR' and OR" of structure XIV are not acid sensitive protective groups.

Compounds of Formula I where $R^1$ is an acylamino group, $G^1$ is null, $G^2$ is a substituted carbonyl alkyl group, Z is —N[C(=O)$R^9$]— and X is a carboxylic acid can be prepared as depicted in Scheme 4.

Scheme 4

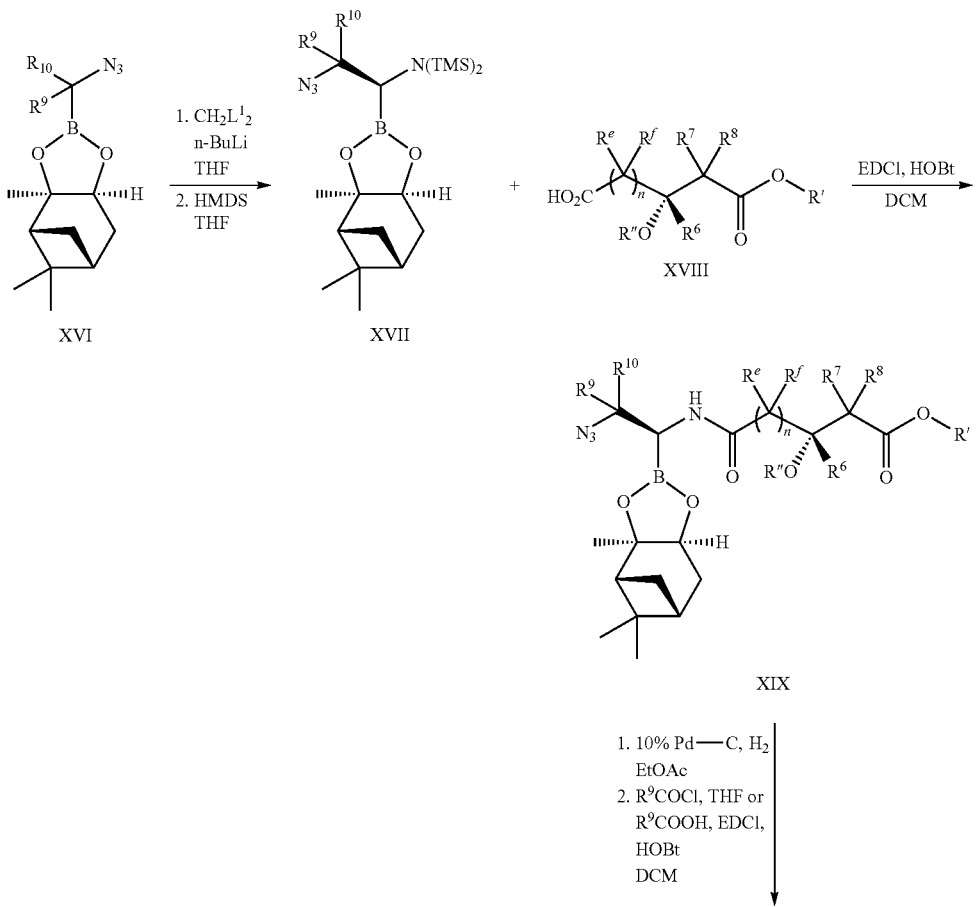

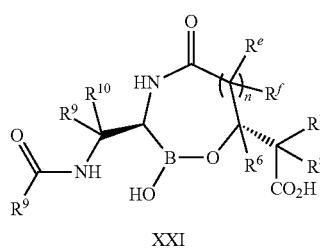

XXI

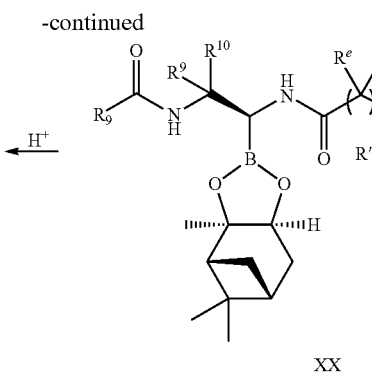

XX

Bis-trimethylsilyl amino intermediate XVII may be made as described above in Scheme 3 starting from azidomethylene boronate XVII [*J. Organomet. Chem.* (2008), 693, 2258-2262]. These derivatives as XVII can be directly utilized in amide coupling reactions with carboxylic acid intermediates of structure XVIII. Such intermediates of structure XVIII with suitable protective groups, where n is 0 or 1 can be obtained by procedures described earlier in both enantiomeric forms [WO0691771, *J. Org. Chem.* (1989), 54, 2085-2091]. Resulting azido-amides of structure XIX from amide coupling reaction can be then further transformed to bis-amide XX. Such transformation may be achieved by reduction via hydrogenation conditions in presence of a palladium catalyst followed by acylation of the resulting amine to XX. Final deprotection-cyclization to compounds of formula XXI may be achieved in single step or sequentially based on the choice of OR' and OR" groups of XVIII as described above.

Compounds of Formula XXVII and XXVIII can be made following the sequence depicted in Scheme 5.

Scheme 5

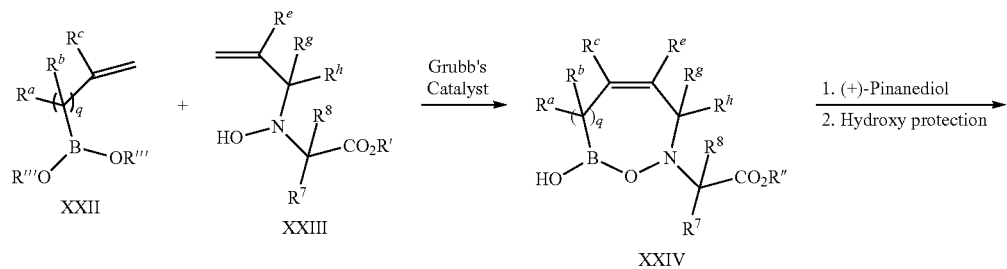

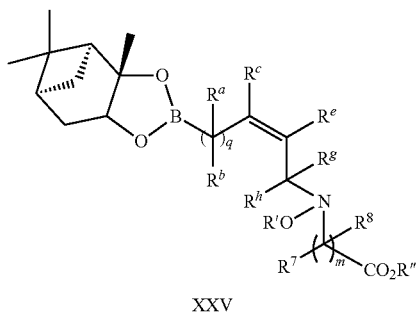

XXV

Matteson-Type Homologation-Amide formation
1. DCM
   n-BuLi, THF
2. LiHMDS
3. $R^9$COCl
   or $R^9CO_2H$, EDCI
   HOBt

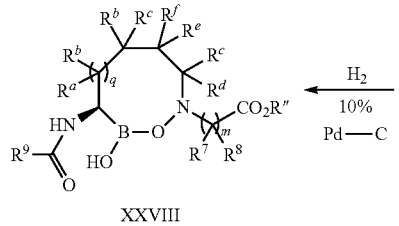 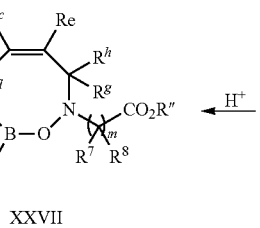 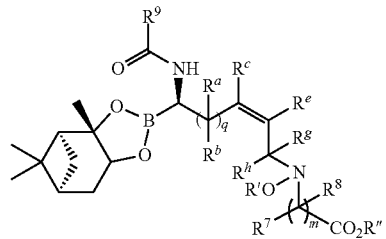

XXVIII    XXVII    XXVI

Ring-Closing Metathesis reaction (RCM) with commercially available boronated olefins (XXII) and olefin substituted hydroxylamine esters (XXIII) result in cyclic boronates of formula XXIV [*Angew. Chem. Int. Ed.* (2002), 41, 152-154]. Such substituted hydroxylamine acetic acid esters (XXIII) may be made by alkenylation of known intermediates [*J. Org. Chem.* (2005), 70, 10494-10501]. Cyclic boronates (XXIV) undergo ready esterification with chiral pinane diol of choice to give required Matteson reaction precursors, upon protection of the resulting alcohol with groups such as t-butyldimethylsilyl- or benzyl or trityl. Matteson-Type homologation followed by amide formation result in compounds of formula XXVI with high stereoselectivity, as described above in Scheme 1. Acid mediated hydrolysis of compounds of XXVI upon deprotection give cyclic boronate (XXVII). Double bond substitution of XXVII can be further modified to other analogs or to a saturated cyclic boronate (XXVIII) by catalytic hydrogenation. The above sequence can be utilized to make 7- or 8-membered rings with double bond by varying XXII where q is 0 or 1.

Compounds of Formula I where $R^1$ is an acylamino group, $G^1$ is null, $G^2$ is a substituted alkyl carbonyl group, Z is —$C(R^9R^{10})$—, Y is N and X is a carboxylic acid can be prepared as depicted in Scheme 6.

Scheme 6

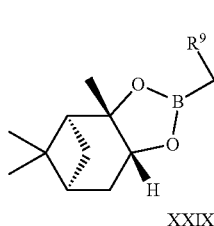

XXIX

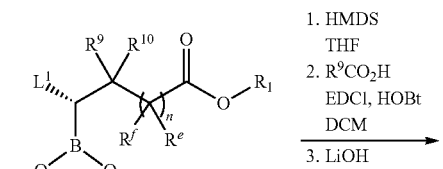

XXX

1. HMDS
   THF
2. $R^9CO_2H$
   EDCl, HOBt
   DCM
3. LiOH
   THF-water

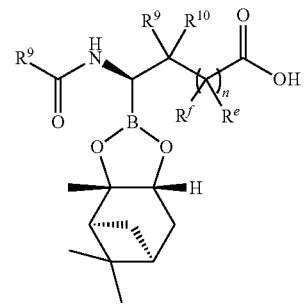

XXXI

EDCl, HOBt
THF

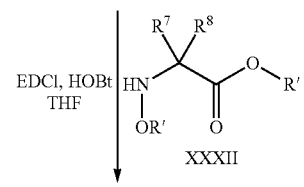

XXXII

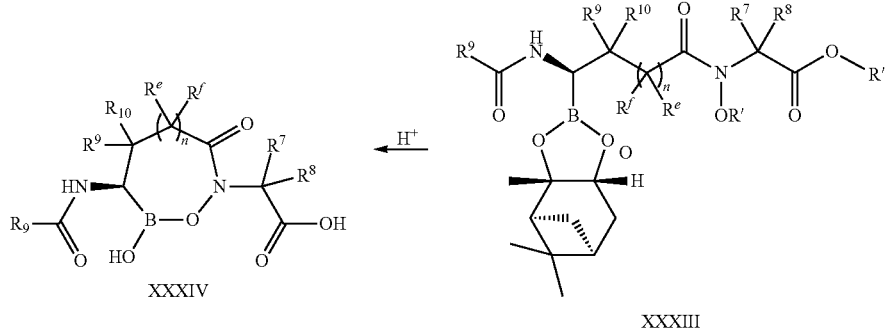

Synthesis of compounds of structure XXXIV can be attained starting from known intermediates of structure XXX (n is 0 or 1), in racemic or enantiomerically pure form. Matteson-Type homologation of XXIX [*Tetrahedron Lett.* (1987), 28, 4499-4502] followed by amination and amide formation result in ester derivative of XXXI. Such ester can hydrolysed under mild conditions to give the corresponding carboxylic acid (XXXI). Alternatively, such carboxylic acids can also be made in racemic form via azido substitution sequence [U.S. Pat. No. 6,586,615; *J. Org. Chem.* (2001), 66, 6375-6380]. Amide formation of substituted and β-hydroxylamine esters with suitable protective groups (—OR' as silyloxy or benzyloxy) result in the formation of compounds of structure XXXIII [*J. Chem. Soc., Perkin Trans* 1, (1989), 2, 235-9]. Cyclic boronate compounds of formula XXXIV can be obtained by deprotection-cyclization of compounds of formula XXXIII, in single step or sequentially based on the choice of OR' and OR" groups. Enantiomercally pure compounds of XXXIV can also be attained by chiral chromatography of the racemic precursors or the final compounds.

The syntheses of compounds of Formulae VII, XIX, XV and XXI in the above sequences are described for trans-isomers. These methods can also be utilized to make cis-isomers in enantiomerically pure form by starting (as in Schemes 1 to 4) with corresponding enantiomer.

Compounds of Formula I where X is a carboxylic acid isostere can be prepared following the protocols described earlier in literature [*J. Med. Chem.* (2011), 54, 2529-2591].

Illustrative Compound Examples

Synthesis of 2-((3R)-2-hydroxy-3-(2-(thiophen-2-yl)acetamido)-1,5,2-dioxaborepan-7-yl)acetic acid. An example synthesis of 1 is depicted in Scheme 7 and Example 1.

Scheme 7

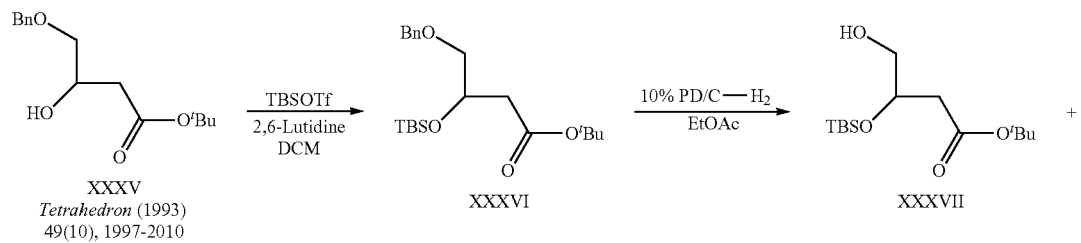

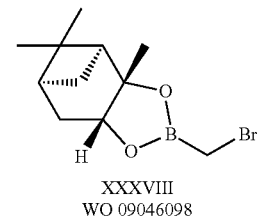

XXXVIII
WO 09046098 n-BuLi
THF

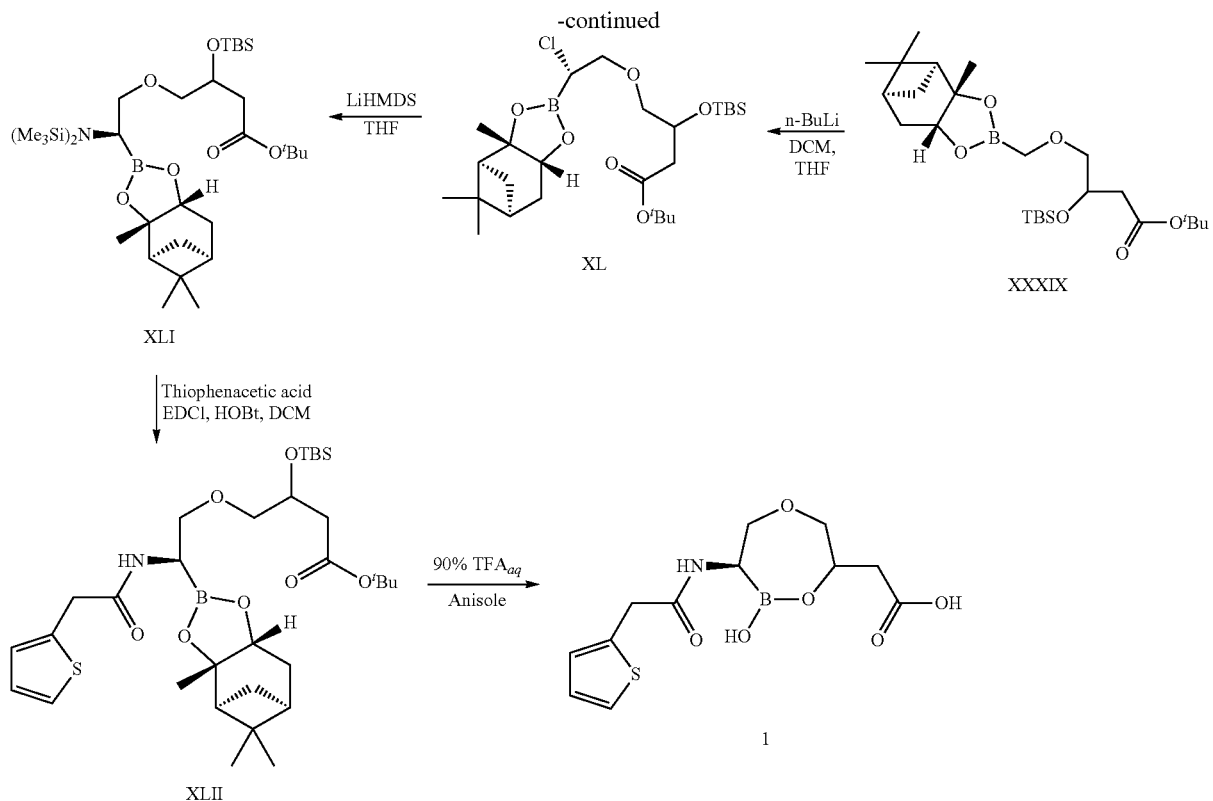

Example 1

Step 1

To a solution of tert-butyl-4-(benzyloxy)-3-hydroxybutanoate XXXV [*Tetrahedron* (1993), 49(10), 1997-2010] (2.3 g, 8.84 mmol) in DCM (100 mL) at 0° C. was added 2,6-lutidine (3.07 mL, 26.52 mmol) and TBSOTf (4 mL, 4. 17.68 mmol). After stirring for 16 h at 0° C., the reaction was diluted with EtOAc (400 mL). The mixture was washed with 1N HCl, saturated aq NaHCO₃, water and dried. The extract was dried (MgSO4) and concentrated under reduced pressure. Purification of the crude product by column chromatography (100% hexane→25% EtOAc/hexane) afforded tert-butyl 4-(benzyloxy)-3-(tert-butyldimethylsilyloxy)butanoate XXXVI (3.1 g, 8.15 mmol, 92.1% yield) as a colorless oil.

Step 2

To a solution of tert-butyl 4-(benzyloxy)-3-(tert-butyldimethylsilyloxy) butanoate XXXVI (3.1 g, 8.15 mmol) in EtOAc (200 mL) under a nitrogen atmosphere was added 10% palladium on carbon (600 mg). The reaction flask was evacuated and then charged with a balloon of hydrogen. The reaction mixture was then stirred at room temperature for 16 h before being filtered through Celite. The filtrate was then concentrated under reduced pressure. Purification of the crude product by column chromatography (100% DCM→50% EtOAc/DCM) afforded tert-butyl 3-(tert-butyldimethylsilyloxy)-4-hydroxybutanoate XXXVII (2.1 g, 7.22 mmol, 88.7% yield) as a colorless oil.

Step 3

To a solution of tert-butyl 3-(tert-butyldimethylsilyloxy)-4-hydroxybutanoate XXXVII (1 g mL, 3.44 mmol) in anhydrous THF (15 mL) at −78° C. with an acetone/dry ice bath was added n-BuLi (2.5 M in hexanes, 1.38 mL, 3.44 mmol) slowly. The mixture was stirred at −78° C. for 15 min. DMSO (0.25 mL, 3.44 mmol) was added dropwise followed by bromide intermediate XXXVIII (WO 09046098) (937 g, 3.44 mmol). The reaction was allowed to reach room temperature slowly and then was heated at 50° C. overnight. The reaction mixture was then diluted with diethyl ether (200 mL) and washed with aqueous HCl (0.6 N, 200 mL). The aqueous layer was re-extracted with diethyl ether (2×100 mL). The organic layers were combined and concentrated in vacuo. Purification of the crude oil by flash chromatography (100% hexane→25% EtOAc/hexane) afforded alkoxy intermediate XXXIX (460 mg, 0.95 mmol, 27.7% yield) as a colorless oil.

Step 4

To a solution of DCM (0.13 mL, 2.15 mmol) in THF (5 mL) at −100° C. was added 2.5 M n-butyl lithium in hexane (0.64 mL, 1.61 mmol) slowly under nitrogen and down the inside wall of the flask, maintaining the temperature below −90° C. The resulting white precipitate was stirred for 30 minutes before the addition of alkoxy intermediate XXXIX from step 3 (520 mg, 1.078 mmol) in THF (2 mL) at −90° C. Zinc chloride (3.77 mL, 1M in diethyl ether, 3.77 mmol) was then added to the reaction mixture at −90° C. and then the reaction was allowed to warm to room temperature where it was stirred for 16 h. The reaction was quenched with a saturated solution of ammonium chloride and the phases were separated. The aqueous phase was then extracted with diethyl ether (3×20 mL) and the combined organic extracts were dried over Na₂SO₄, filtered and concentrated under reduced pressure. The concentrated material was then chromatographed (100% hexane→50% EtOAc-hexane) to obtain the chloromethylenation product XL (280 mg, 0.53 mmol, 48.9% yield).

Step 5

Chloro intermediate XL (260 mg, 0.48 mmol) in THF (4 mL) was cooled to −78° C. under nitrogen. A solution of 1M LiHMDS solution in THF (0.5 mL, 0.5 mmol) was added slowly at −78° C. Upon completion of the addition, the reaction flask was allowed to warm to room temperature. After stirring at room temperature for 16 h, the reaction mixture was concentrated under vacuum and hexane (20 mL) was added. The precipitated lithium salts were filtered off through a Celite pad, rinsed with additional hexane and the combined filtrates were concentrated under vacuum to give crude bis(trimethylsilyl)amine product XLI.

Step 6

To a stirred solution of 2-thiophenacetic acid (80 mg, 0.57 mmol) in DCM (10 mL) at 0° C. under nitrogen was added EDCI (137 mg, 0.72 mmol) and HOBT (77 mg, 0.57 mmol). After stirring at 0° C. for 30 minutes, a solution of the crude bis-silyl amide (XLI) intermediate in DCM (5 mL) followed by N-methyl-morpholine (0.1 mL, 0.98 mmol) were sequentially added at 0° C. Upon completion of the addition, the reaction flask was allowed to warm to room temperature. After stirring at room temperature overnight, the reaction mixture was washed with water, dried and concentrated under vacuum. The residue was purified by column chromatography (100% DCM→25% EtOAc/DCM) to afford amide XLII (100 mg, 0.157 mmol, 32.7% yield for 2 steps).

Step 7

A solution of amide XLII (50 mg, 0.078 mmol) in anisole (2.5 mL) at 0° C. was treated with pre-cooled 90% aq trifluoroacetic acid (10 mL). The reaction mixture was warmed to room temperature and stirred for 16 h. The mixture was evaporated in vacuo, azeotroped with MeCN (3×5 mL). The residue was sonicated in water (10 mL) and ether (10 mL). The aqueous phase was separated, washed with ether (2×5 mL) and freeze dried to give fluffy solid 2-(3R)-2-hydroxy-3-(2-(thiophen-2-yl)acetamido)-1,5,2-dioxaborepan-7-yl) acetic acid 1 (15 mg, 0.48 mmol, 61.4% yield). $^1$H NMR (CD$_3$OD) δ ppm 6.98-7.00 (m, 1H), 7.00-7.09 (m, 1H), 7.33-7.35 (m, 1H) (partial $^1$H NMR spectral data of the isomeric mixture of compound 1). ESIMS found for $C_{12}H_{16}BNO_6S$ m/z 296 (M−H$_2$O)$^+$.

Synthesis of 2-(3R)-5-acetyl-2-hydroxy-3-(2-(thiophen-2-yl)acetamido)-1,5,2-oxazaborepan-7-yl)acetic acid. An example synthesis of 10 is depicted in Scheme 8 and Example 2.

Scheme 8

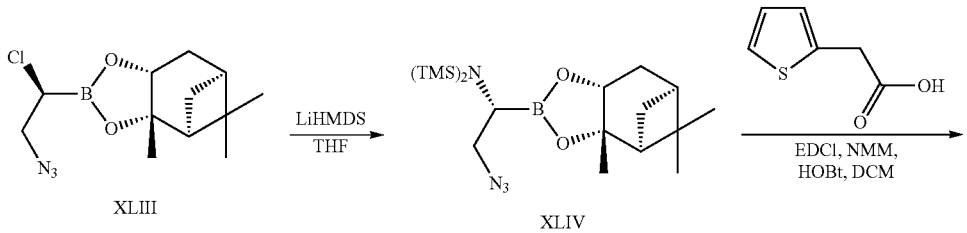

XLIII

J. Organomet. Chem. (2008) 693(13), 2258-2262

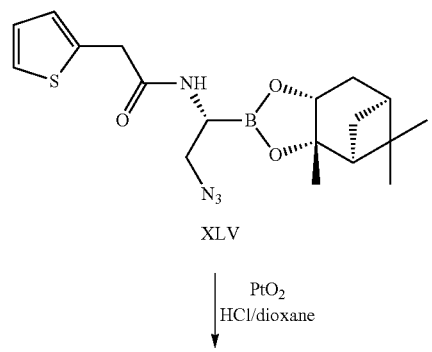

XLV

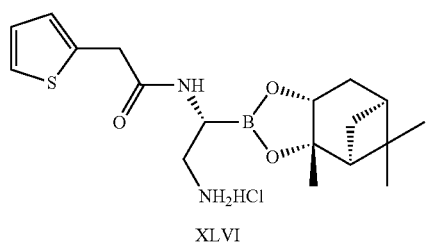
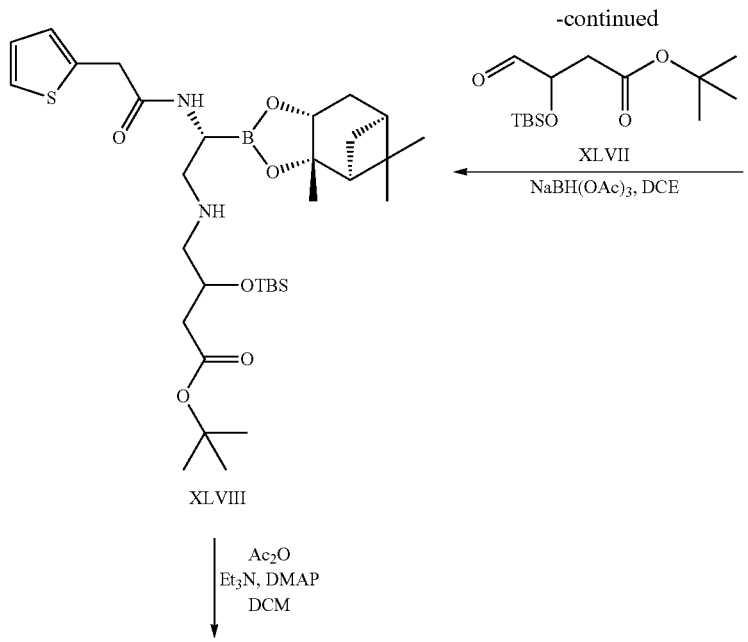
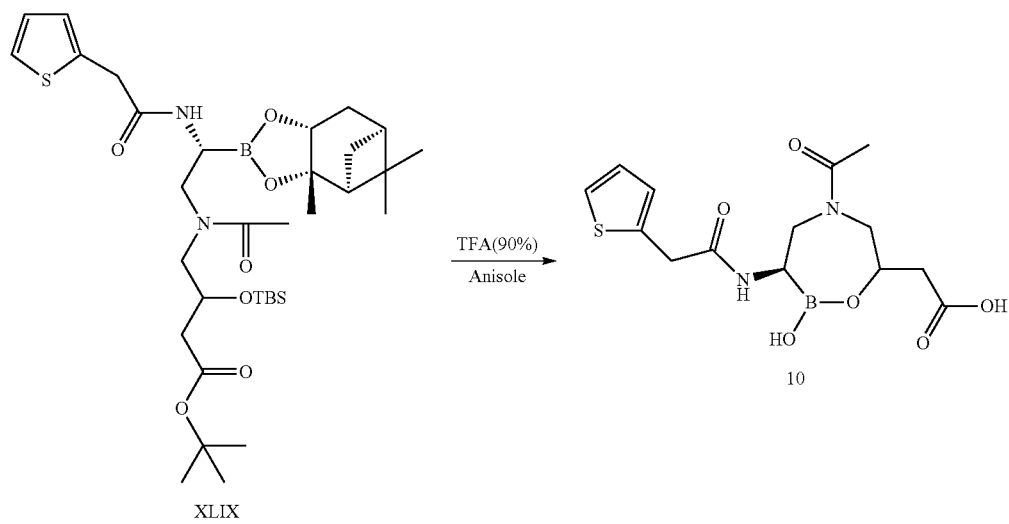 [SMILES: CC(=O)N(CC(CC(=O)OC(C)(C)C)O[Si](C)(C)C(C)(C)C)C[C@H](NC(=O)Cc1cccs1)B1O[C@@H]2C[C@@H]3C[C@@H](C3(C)C)[C@]2(C)O1 ; CC(=O)N1CC(CC(=O)O)OB(O)[C@@H](NC(=O)Cc2cccs2)C1]

Example 2

Step 1

To the solution of compound XLIII (5.00 g, 17.6 mmol, 1.0 eq) in THF (anhydrous, 50 mL) was added LiHMDS solution (23.0 mL, 1.0 M in hexane, 1.3 eq) at 78° C. in 15 minutes. The resulting solution was slowly warmed up to room temperature in three hours and stirred for overnight. The reaction solution was concentrated to dryness. The residue was diluted with hexanes and the suspension was filtered though a pad of Celite. The filtrate was concentrated to give crude compound XLIV as an orange oil (4.91 g), which was directly used for next step without further purification.

Step 2

To the solution of 2-thiopheneacetic acid (2.05 g, 14.4 mmol, 1.2 eq) in DCM (100 mL) was added EDCI (3.45 g, 18.0 mmol, 1.5 eq) at 0° C., followed by HOBt (2.21 g, 14.4 mmol, 1.2 eq). The resulting mixture was stirred at 0° C. for 30 minutes before crude compound XLIV (4.91 g in 100 mL DCM) was added, followed by N-methylmorpholine (3.96 mL, 36.0 mmol, 3.0 eq). The reaction mixture was warmed up to room temperature and stirred for overnight. The reaction mixture was concentrated to dryness. The residue was purified by flash column chromatography (silica, DCM/EtOAc=5:1) to give compound XLV (3.50 g, 8.14 mmol, 52.0% yield for 2 steps) as a slightly yellow solid. $^1$H NMR (300 MHz, CDCl$_3$) δ ppm 0.84 (s, 3H), 1.25 (s, 3H), 1.35 (d, 1H), 1.38 (s, 3H), 1.58-1.66 (m, 1H), 1.82-2.05 (m, 2H), 2.10-2.40 (m, 2H), 2.40-2.52 (m, 1H), 2.92 (td, 1H), 3.41 (dd, 1H), 3.62 (dd, 1H), 3.92 (s, 2H), 4.24 (dd, 1H), 6.62 (brs, 1H), 6.95-7.00 (m, 1H), 7.01-7.06 (m, 1H), 7.28-7.33 (m, 1H). ESIMS found for C$_{18}$H$_{25}$BN$_4$O$_3$S m/z 389.2 (M+H)$^+$.

Step 3

A suspension of compound XLV (2.00 g, 5.15 mmol) and PtO$_2$ (200 mg) in HCl/dioxane (4.0 M, 40 mL) was degassed 3 time. The suspension was stirred with H$_2$ at 60 psi for overnight. The reaction mixture was filtered though a pad of Celite and the filtrate was concentrated to dryness. The residue was treated with diethyl ether to precipitate compound XLVI as an off-white solid (2.10 g, 5.15 mmol, quantitative yield). ESIMS found for C$_{18}$H$_{28}$BClN$_2$O$_3$S m/z 363.2 (M−HCl+H)$^+$.

Step 4

A solution of compound XLVI (200 mg, 0.552 mmol, 1.0 eq) and 3-(tert-butyl-dimethyl-silanyloxy)-4-oxo-butyric acid tert-butyl ester (XLVII) (made from XXXVII of Scheme 7 following oxidation procedure described as in *J Org. Chem.* (1999), 64, 5447-5452) (159 mg, 0.552 mmol, 1.0 eq) in 1,2-dichloroethane (3 mL) was treated with NaBH(OAc)$_3$ (234 mg, 1.10 mmol, 2.0 eq) for 10 min. The reaction mixture was diluted with EtOAc and washed with sodium bicarbonate. The organic phase was separated, dried, and concentrated to dryness, affording compound XLVIII (330 mg, 0.52 mmol, 94.2% yield). ESIMS found for C$_{32}$H$_{55}$BN$_2$O$_6$SSi m/z 635.2 (M+H)$^+$.

Step 5

Crude compound XLVIII (0.5 mmol, 1.0 eq) and Et$_3$N (0.15 mL, 1.1 mmol, 2.2 eq) in DCM (5 mL) was treated with acetic anhydride (56 pt, 0.60 mmol, 1.2 eq) at 0° C. followed by catalytic amount of DMAP (5 mg). The resulting mixture was stirred at 0° C. for 30 minutes and warmed up to room temperature for 16 h. The reaction mixture was concentrated, Chromatographed on a silica column eluting with (100% DCM→30% EtOAc/DCM) to afford compound XLIX (40 mg, 0.059 mmol, 11.8% yield). ESIMS found for C$_{35}$H$_{59}$BN$_2$O$_6$SSi m/z 675.6 (M+H)$^+$.

Step 6

A solution of amide XLIX (39 mg, 0.057 mmol) in anisole (2.5 mL) at 0° C. was treated with pre-cooled 90% aq TFA (5 mL). The reaction mixture was warmed to room temperature and stirred for 16 h. The mixture was evaporated in vacuo, azeotroped with MeCN (3×5 mL). The residue was sonicated in water (10 mL) and ether (10 mL). The aqueous phase was separated, washed with ether (2×5 mL) and freeze dried to give 2-((3R)-5-acetyl-2-hydroxy-3-(2-(thiophen-2-yl)acetamido)-1,5,2-oxazaborepan-7-yl)acetic acid (10) as a white solid (8 mg, 0.023 mmol, 39.6% yield). $^1$H NMR (CD$_3$OD) δ ppm 6.95-7.05 (m, 2H), 7.33-7.37 (m, 1H), (partial $^1$H NMR spectral data of the isomeric mixture of compound 10). ESIMS found for C$_{14}$H$_{19}$BN$_2$O$_6$S m/z 355 (M+H)$^+$.

Synthesis of 2-(3R)-2-hydroxy-5-(methoxycarbonyl)-3-(2-(thiophen-2-yl)acetamido)-1,5,2-oxazaborepan-7-yl)acetic acid. An example synthesis of 46 is depicted in Scheme 9 and Example 3.

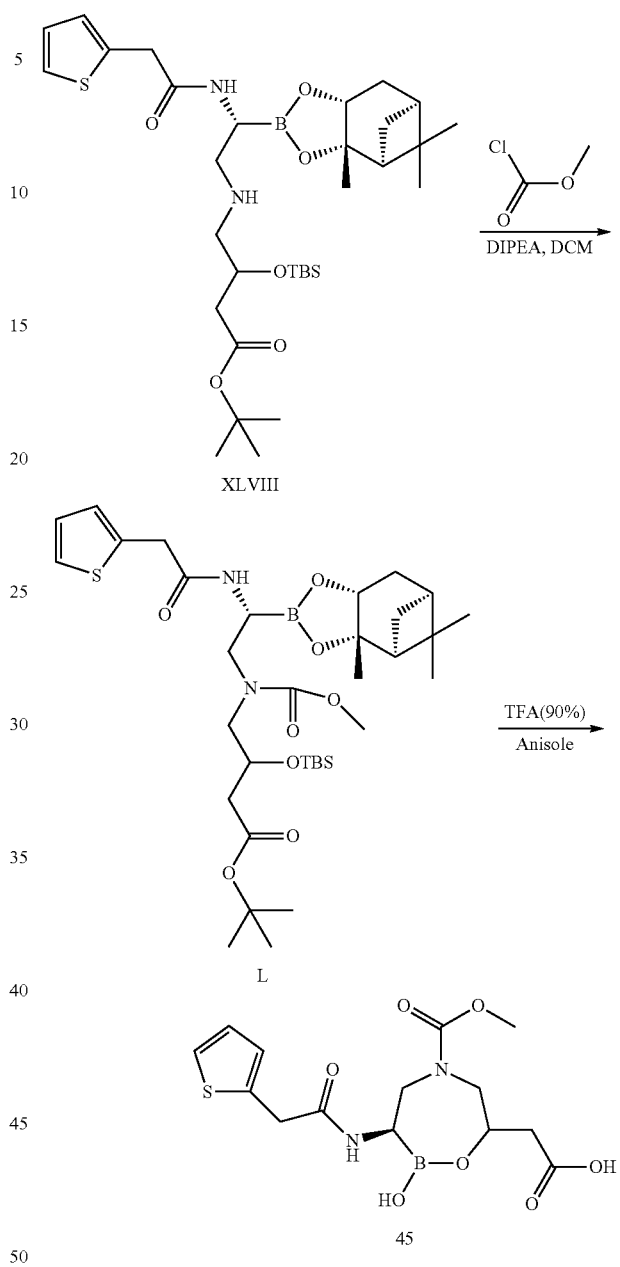

Scheme 9

Example 3

Step 1

Compound XLVIII (160 mg, 0.252 mmol, 1.0 eq) and DIPEA (125 pt, 0.756 mmol, 3.0 eq) in DCM (2 mL) was treated with methyl chloroformate (39 pt, 0.50 mmol, 2.0 eq) at 0° C. The resulting mixture was stirred at 0° C. for 30 minutes and warmed up to room temperature for 1 h. The reaction mixture was concentrated to afford compound L which was directly used for next step without further purification. ESIMS found for C$_{34}$H$_{57}$BN$_2$O$_8$SSi m/z 693.2 (M+H)$^+$.

Step 2

Crude compound L in anisole (1 mL) was treated with TFA (90% in water) at room temperature overnight. The mixture was concentrated to dryness. The residue was purified by prep. HPLC to give 2-(3R)-2-hydroxy-5-(methoxycarbonyl)-3-(2-(thiophen-2-yl)acetamido)-1,5,2-oxazaborepan-7-yl)acetic acid (45) as a white solid (11 mg, 0.030 mmol, 11.8% yield for 2 steps). $^1$H NMR (300 MHz, CD$_3$OD) δ ppm 2.38-2.49 (m, 2H), 2.69-2.92 (m, 4H), 3.55-3.58 (m, 2H), 4.02-4.18 (m, 5H), 7.01-7.06 (m, 2H), 7.37-7.40 (m, 1H). ESIMS found for $C_{14}H_{19}BN_2O_7S$ m/z 371.2 (M+H)$^+$.

Illustrative compounds of Formula (I) are shown in Table 1. Some structures are shown with defined configurations at selected stereocenters but the shown stereochemistries are not meant to be limiting and all possible stereoisomers of the shown structures are to be considered encompassed herein. Compounds of any absolute and relative configurations at the stereocenters as well as mixtures of enantiomers and diastereoisomers of any given structure are also encompassed herein.

TABLE 1

| Example | Structure |
|---|---|
| 1 | 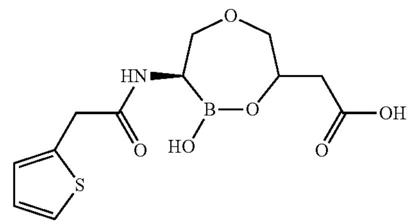 [SMILES: O=C(O)CC1COC[C@H](NC(=O)Cc2cccs2)B(O)O1] |
| 2 | 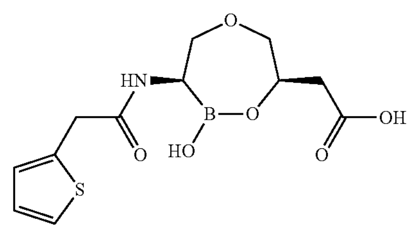 [SMILES: O=C(O)C[C@@H]1COC[C@H](NC(=O)Cc2cccs2)B(O)O1] |
| 3 | 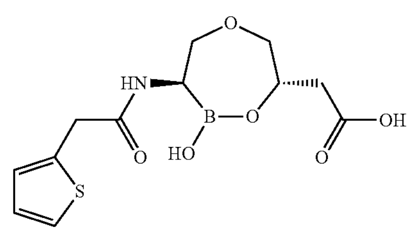 |
| 4 | 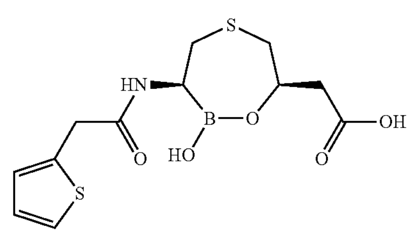 |
| 5 | 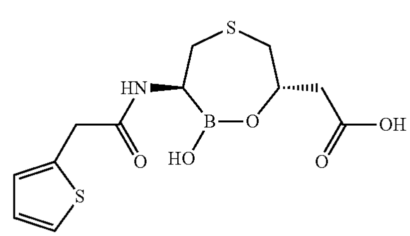 [SMILES: O=C(O)C[C@H]1CSC[C@H](NC(=O)Cc2cccs2)B(O)O1] |

TABLE 1-continued

| Example | Structure |
| --- | --- |
| 6 | (structure) |
| 7 | (structure) |
| 8 | (structure) |
| 9 | (structure) |
| 10 | (structure) |
| 11 | (structure) |

TABLE 1-continued

| Example | Structure |
|---|---|
| 12 | (structure) |
| 13 | (structure) |
| 14 | (structure) |
| 15 | (structure) |
| 16 | (structure) |
| 17 | (structure) |

TABLE 1-continued

| Example | Structure |
|---|---|
| 18 | (structure) |
| 19 | (structure) |
| 20 | (structure) |
| 21 | (structure) |
| 22 | (structure) |

TABLE 1-continued

| Example | Structure |
|---|---|
| 23 | (structure: pyridine N-oxide-CH2-C(=O)-NH-[7-membered boronate ring with CH2COOH], B-OH) |
| 24 | (structure: thiophene with C(=CHCOOH)-C(=O)-NH-[7-membered boronate ring with CH2COOH], B-OH) |
| 25 | (structure: thiophene with C(=CH-CH2OH)-C(=O)-NH-[7-membered boronate ring with CH2COOH], B-OH) |
| 26 | (structure: thiophene-C(=N-OCH3)-C(=O)-NH-[7-membered boronate ring with CH2COOH], B-OH) |
| 27 | (structure: thiophene-C(=N-O-CH3)-C(=O)-NH-[7-membered boronate ring with CH2COOH], B-OH) |
| 28 | (structure: thiophene-C(=N-O-CH2-(2-carboxyphenyl))-C(=O)-NH-[7-membered boronate ring with CH2COOH], B-OH) |

TABLE 1-continued

| Example | Structure |
|---------|-----------|
| 29 | 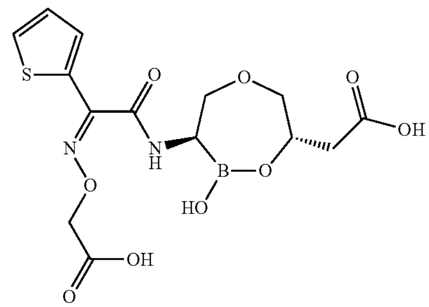 [SMILES: O=C(O)CO/N=C(\C(=O)N[C@H]1COC[C@H](CC(=O)O)OB1O)c1cccs1] |
| 30 | 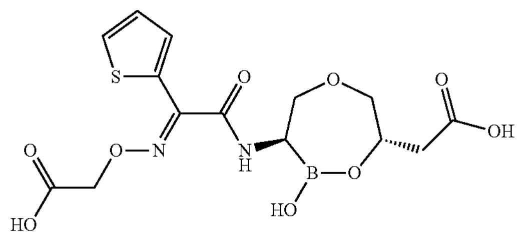 [SMILES: O=C(O)CO/N=C(/C(=O)N[C@H]1COC[C@H](CC(=O)O)OB1O)c1cccs1] |
| 31 | 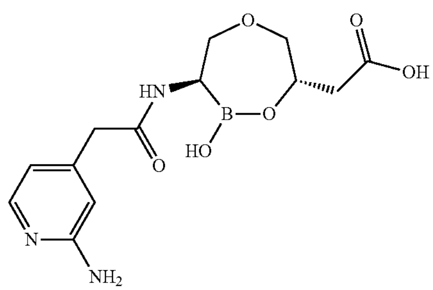 |
| 32 | 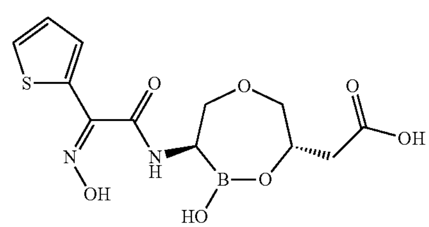 [SMILES: O=C(O)C[C@H]1COC[C@H](NC(=O)/C(=N\O)c2cccs2)B(O)O1] |
| 33 | 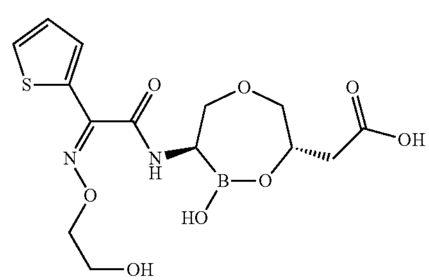 [SMILES: O=C(O)C[C@H]1COC[C@H](NC(=O)/C(=N\OCCO)c2cccs2)B(O)O1] |

TABLE 1-continued

| Example | Structure |
|---|---|
| 34 | 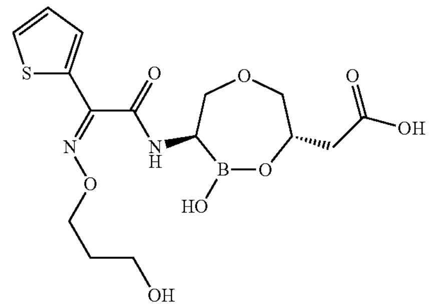 [SMILES: O=C(O)C[C@H]1COC[C@H](NC(=O)/C(=N\OCCCO)c2cccs2)B(O)O1] |
| 35 | 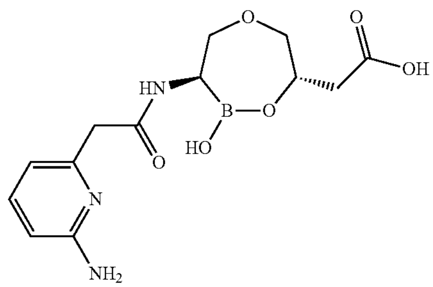 [SMILES: Nc1cccc(CC(=O)N[C@H]2COC[C@H](CC(=O)O)OB2O)n1] |
| 36 | 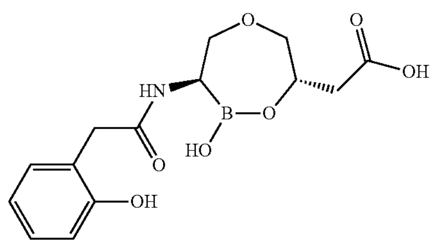 [SMILES: O=C(O)C[C@H]1COC[C@H](NC(=O)Cc2ccccc2O)B(O)O1] |
| 37 | 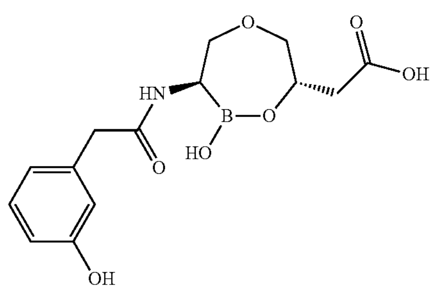 [SMILES: O=C(O)C[C@H]1COC[C@H](NC(=O)Cc2cccc(O)c2)B(O)O1] |
| 38 | 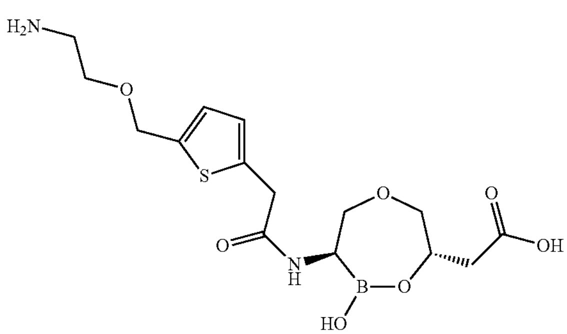 [SMILES: NCCOCc1ccc(CC(=O)N[C@H]2COC[C@H](CC(=O)O)OB2O)s1] |

TABLE 1-continued

| Example | Structure |
|---|---|
| 39 | (structure) |
| 40 | (structure) |
| 41 | (structure) |
| 42 | (structure) |
| 43 | (structure) |
| 44 | (structure) |
| 45 | (structure) |

Example 4

Selected β-lactamase inhibitors were tested for their ability to potentiate the monobactam tigemonam. The potentiation effect is observed as the ability of BLI compounds to inhibit growth in the presence of sub-inhibitory concentration of tigemonam. MIC of test strains vary from 8 μg/mL to >128 μg/mL. Tigemonam is present in the test medium at 4 μg/mL. Compounds tested at the highest concentration of 40 μg/mL. In this assay potency of compounds is determined as a concentration of BLIs to inhibit growth of bacteria in the presence of 4 μg/mL of aztreonam ($MPC_{@4}$). Tables 2 and 3 summarize BLI potency of tigemonam potentiation ($MPC_{@4}$) for various strains overexpressing class A (ESBLs), class C and class D β-lactamases, respectively. Tigemonam MIC for each strain is also shown. Table 2 summarizes activity of BLIs to potentiate tigemonam against strains expressing class A ESBLs. Table 3 summarizes activity of BLIs to potentiate Tigemonam against strains expressing class C and D enzymes.

TABLE 2

| | Tigemonam MIC (μg/mL) | | | | | | | |
|---|---|---|---|---|---|---|---|---|
| | 512 | 256 | >512 | 256 | 64 | 256 | >512 | 512 |
| | $MPC_4$ | $MPC_4$ | $MPC_4$ | $MPC_4$ | $MPC_4$ | $MPC_4$ | $MPC_4$ | $MPC_4$ |
| | CTX-M-14 | CTX-M-15 | SHV-5 | SHV-12 | SHV-18 | TEM-10 | TEM-10 | TEM-26 |
| | KP1005 | KP1009 | ec308 | KP1010 | KP1012 | EC1009 | ec302 | ec304 |
| Tazobactam | 10 | 10 | 5 | 1.25 | 1.25 | 2.5 | 5 | 1.25 |
| Clavulanic Acid | 2.5 | 1.25 | <=0.6 | <=0.6 | <=0.6 | <=0.6 | 2.5 | <=0.6 |
| 1 | Y | Y | Y | X | X | Z | Z | Z |
| 10 | Y | Y | Y | X | ND | ND | Z | ND |
| 45 | Y | Y | Y | X | ND | ND | Z | ND |

X = $MPC_{@4}$ of less than 2 μg/mL.
Y = $MPC_{@4}$ of 2 μg/mL to 10 μg/mL.
Z = $MPC_{@4}$ of greater than 10 μg/mL.
ND = Not Determined.

TABLE 3

| | Class | | | | |
|---|---|---|---|---|---|
| | C | C | C | D | D |
| | Tigemonam MIC (μg/mL) | | | | |
| | 32 | 16 | 8 | 256 | 8 |
| | $MPC_4$ | $MPC_4$ CMY-6, | $MPC_4$ | $MPC_4$ OXA-10, | $MPC_4$ OXA-2, |
| | ECL1002 | EC1010 | PAM2035 | KP1007 | KPX1001 |
| Tazobactam | 10 | 2.5 | 5 | 5 | 40 |
| Clavulanic Acid | >40 | 40 | >40 | <=0.6 | 1.25 |
| 1 | Y | X | Y | Y | X |
| 10 | Y | Y | ND | X | ND |
| 45 | Z | Y | ND | X | ND |

X = $MPC_{@4}$ of less than 2 μg/mL.
Y = $MPC_{@4}$ of 2 μg/mL to 10 μg/mL.
Z = $MPC_{@4}$ of greater than 10 μg/mL.
ND = Not Determined.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials that are susceptible to modifications, as well as alterations in the fabrication methods and equipment. Such modifications will become apparent to those skilled in the art from a consideration of this disclosure or practice of the methods disclosed herein. Consequently, it is not intended that this invention be limited to the specific embodiments disclosed herein, but that it cover all modifications and alternatives coming within the true scope and spirit of the invention.

What is claimed is:

1. A compound having the structure of formula I:

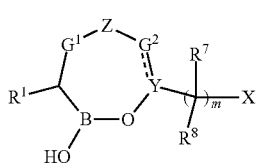

or pharmaceutically acceptable salt thereof, wherein:

$R^1$ is selected from a group consisting of —N($R^9$)C(=O)$R^9$, —N($R^9$)C(=O)NR$^9$R$^{10}$, —N($R^9$)C(=O)OR$^9$, —N($R^9$)C(=O)C(=NR$^{10}$)R$^9$, —N($R^9$)C(=O)C(=CR$^9$R$^{10}$)R$^9$, —N($R^9$)C(=O)C$_{1-4}$alkylN($R^9$)C(=O)R$^9$, —N($R^9$)C(=NR$^{10}$)R$^9$, —C(=NR$^{10}$)NR$^9$R$^{10}$, —N=C($R^9$)NR$^9$R$^{10}$, —N($R^9$)SO$_2$R$^9$, —N($R^9$)SO$_2$NR$^9$R$^{10}$, —N=CHR$^9$, —C($R^9$R$^{10}$)C(=O)NR$^9$R$^{10}$, —C($R^9$R$^{10}$)N($R^9$)C(=O)R$^9$;

$G^1$ is selected from a divalent group consisting of —C($R^aR^b$)—, —C(=$R^{a'}$)—, —C($R^aR^b$)C($R^cR^d$)—, —C($R^a$)=C($R^c$)—, —C(=O)C($R^aR^b$)—, —C($R^aR^b$)C(=O)—, and a bond;

$G^2$ is selected from a divalent group consisting of —C($R^eR^f$)—, —C(=$R^{e'}$)—, =C($R^e$)—, —C($R^eR^f$)C($R^gR^h$)—, —C($R^eR^f$)C($R^gR^h$)C($R^iR^j$)—, —C(=O)—, —C(=O)C($R^eR^f$)—, —C($R^eR^f$)C(=O)—, —C(=O)C($R^eR^f$)C($R^gR^h$)—, —C($R^eR^f$)C($R^gR^h$)C(=O)—, —C(=O)C($R^eR^f$)C($R^gR^h$)C($R^iR^j$)—, —C($R^eR^f$)C($R^gR^h$)C($R^iR^j$)C(=O)—, —C($R^e$)=C($R^g$)—, —C($R^e$)=C($R^g$)C($R^iR^j$)— and —C($R^eR^f$)C($R^g$)=C($R^j$)—;

$R^a$, $R^b$, $R^c$, $R^d$, $R^e$, $R^f$, $R^g$, $R^h$, $R^i$, and $R^j$ are independently selected from a group consisting of H, Cl, F, CN, CF$_3$, —R$^9$, —OR$^9$, NR$^9$R$^{10}$, —C(=O)NR$^9$R$^{10}$, and —C(=O)OR$^9$, or independently: $R^a$ and $R^c$, $R^e$ and an $R^7$, $R^e$ and $R^6$, $R^k$ and $R^c$, $R^k$ and $R^e$, $R^e$ and $R^g$, and $R^g$ and $R^j$ are taken together with the atoms to which they are attached and any intervening atoms to form a substituted or unsubstituted aryl, substituted or unsubstituted heteroaryl, substituted or unsubstituted carbocyclyl or substituted or unsubstituted heterocyclyl, or independently $R^e$ and $R^f$ are taken together with the atoms to which they are attached and any intervening atoms to form a substituted or unsubstituted carbocyclyl or substituted or unsubstituted heterocyclyl;

$R^{a'}$ and $R^{e'}$ are =CR$^9$R$^{10}$ or independently $R^{a'}$ and $R^k$, or $R^{e'}$ and $R^k$, are taken together with the atoms to which they are attached to form a substituted or unsubstituted aryl, substituted or unsubstituted heteroaryl, substituted or unsubstituted carbocyclyl, or substituted or unsubstituted heterocyclyl;

Z is selected from a divalent group consisting of —O—, —S—, —N(R$^9$)—, —N[C(=O)R$^9$]—, —N[C(=O)NR$^9$R$^{10}$]—, —N[C(=O)OR$^9$]—, —N[C(=NR$^{10}$)R$^9$]—, —N[SO$_2$R$^9$]—, —N[SO$_2$NR$^9$R$^{10}$]—, —N(R$^9$)C(=O)—, and —N(R$^k$);

$R^k$ and $R^c$, $R^k$ and $R^e$, $R^{a'}$ and $R^k$, or $R^{e'}$ and $R^k$ are taken together with any intervening atoms to form a substituted or unsubstituted aryl, substituted or unsubstituted heteroaryl, substituted or unsubstituted carbocyclyl or substituted or unsubstituted heterocyclyl;

Y is selected from a group consisting of N, CR$^6$, and C, with the proviso that when Z is a bond, —C(R$^9$R$^{10}$)—, —C(R$^9$R$^k$)—, or —C(=R$^k$)—, then Y is N;

$R^6$ is selected from a group consisting of H, —C$_{1-9}$alkyl, —C$_{2-9}$alkenyl, —C$_{2-9}$alkynyl, carbocyclyl, —C$_{1-9}$alkylR$^{11}$, —C$_{2-9}$alkenylR$^{11}$, —C$_{2-9}$alkynylR$^{11}$, carbocyclyl-R$^{11}$, —C(=O)OR$^9$ and —C$_{1-9}$alkylCO$_2$R$^9$, —C$_{2-9}$alkenylCO$_2$R$^9$, —C$_{2-9}$alkynylCO$_2$R$^9$, and -carbocyclyl-CO$_2$R$^9$, or alternatively $R^6$ and an $R^7$ or $R^6$ and $R^e$ are taken together with the atoms to which they are attached and any intervening atoms to form a substituted or unsubstituted carbocyclyl or substituted or unsubstituted heterocyclyl;

each $R^7$ is independently selected from a group consisting of H, halo, —C$_{1-9}$alkyl, —C$_{2-9}$alkenyl, —C$_{2-9}$alkynyl, —NR$^9$R$^{10}$, —OR$^9$, —C$_{1-9}$alkylCO$_2$R$^9$, —C$_{2-9}$alkenylCO$_2$R$^9$, —C$_{2-9}$alkynylCO$_2$R$^9$, and -carbocyclyl-CO$_2$R$^9$, or independently, $R^6$ and an $R^7$ or an $R^7$ and an $R^8$ are taken together with the atoms to which they are attached and any intervening atoms to form a substituted or unsubstituted carbocyclyl or substituted or unsubstituted heterocyclyl, or independently an $R^7$ and $R^e$ are taken together with intervening atoms to form a substituted or unsubstituted aryl, substituted or unsubstituted heteroaryl, substituted or unsubstituted carbocyclyl, or substituted or unsubstituted heterocyclyl;

each $R^8$ is independently selected from a group consisting of H, halo, —C$_{1-9}$alkyl, —C$_{2-9}$alkenyl, —C$_{2-9}$alkynyl, —NR$^9$R$^{10}$, —OR$^9$, —C$_{1-9}$alkylCO$_2$R$^9$, —C$_{1-9}$alkylCO$_2$R$^9$, —C$_{2-9}$alkenylCO$_2$R$^9$, —C$_{2-9}$alkynylCO$_2$R$^9$, and -carbocyclyl-CO$_2$R$^9$, or independently, an $R^7$ and an $R^8$ are taken together with the atoms to which they are attached to form a substituted or unsubstituted carbocyclyl or substituted or unsubstituted heterocyclyl, or independently, each $R^8$ attached to a ring atom forming part of a substituted or unsubstituted aryl or a substituted or unsubstituted heteroaryl is absent;

each $R^9$ is independently selected from a group consisting of H, —C$_{1-9}$alkyl, C$_{2-9}$alkenyl, —C$_{2-9}$alkynyl, carbocyclyl, —C$_{1-9}$alkylR$^{11}$, C$_{2-9}$alkenylR$^{11}$, —C$_{2-9}$alkynylR$^{11}$, -carbocyclyl-R$^{11}$, —C$_{1-9}$alkylCO$_2$R$^{12}$, C$_{2-9}$alkenylCO$_2$R$^{12}$, —C$_{2-9}$alkynylCO$_2$R$^{12}$, -carbocyclyl-CO$_2$R$^{12}$, —C$_{1-9}$alkyl-N(R$^{12}$)OR$^{12}$, C$_{2-9}$alkenyl-N(R$^{12}$)OR$^{12}$, —C$_{2-9}$alkynyl-N(R$^{12}$)OR$^{12}$, -carbocyclyl-N(R$^{12}$)OR$^{12}$, —C$_{1-9}$alkyl-OR$^{12}$, C$_{2-9}$alkenyl-OR$^{12}$, —C$_{2-9}$alkynyl-OR$^{12}$, -carbocyclyl-OR$^{12}$, substituted or unsubstituted aryl, substituted or unsubstituted heteroaryl, substituted or unsubstituted carbocyclyl, and substituted or unsubstituted heterocyclyl;

each $R^{10}$ is independently selected from a group consisting of H, —C$_{1-9}$alkyl, —OR$^9$, —CH(=NH)—, —C(=O)OR$^9$, substituted or unsubstituted aryl, substituted or unsubstituted heteroaryl, substituted or unsubstituted carbocyclyl, and substituted or unsubstituted heterocyclyl;

each $R^{11}$ is independently selected from a group consisting of substituted or unsubstituted aryl, substituted or unsubstituted heteroaryl, substituted or unsubstituted carbocyclyl, and substituted or unsubstituted heterocyclyl;

each $R^{12}$ is independently selected from a group consisting of H, C$_{1-9}$alkyl, —(CH$_2$)$_{0-3}$—R$_{11}$, —C(R$^{13}$)$_2$OC(O)C$_{1-9}$alkyl, —C(R$^{13}$)$_2$OC(O)R$^{11}$, —C(R$^{13}$)$_2$OC(O)OC$_{1-9}$alkyl and —C(R$^{13}$)$_2$OC(O)OR$^{11}$;

each $R^{13}$ is independently selected from a group consisting of H and C$_{1-4}$alkyl;

each X is independently selected from a group consisting of —CO$_2$R$^{12}$, and carboxylic acid isosteres;

m is independently zero or an integer from 1 to 2;

the bond represented by a dashed and solid line represents a bond selected from the group consisting of a single bond and a double bond; and each C$_{1-9}$alkyl, C$_{2-9}$alkenyl, and C$_{2-9}$alkynyl is optionally substituted.

2. The compound of claim 1, having the defined stereochemistry at 3-position shown in formula Ia:

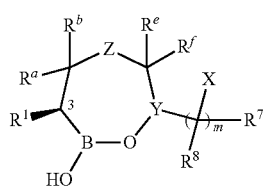

or a pharmaceutically acceptable salt thereof.

3. The compound of claim 1 wherein Y is CR$^6$, having the defined 3,7-trans-stereochemistry shown in formula Ib:

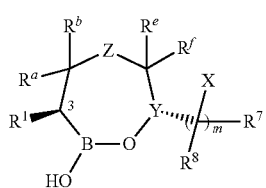

or a pharmaceutically acceptable salt thereof.

4. The compound of claim 1 wherein Y is CR$^6$, having the defined 3,7-cis-stereochemistry shown in formula Ic:

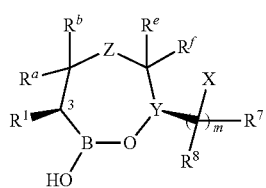

or a pharmaceutically acceptable salt thereof.

5. The compound of claim 1, wherein R$^1$ is —NHC(=O)R$^9$.

6. The compound of claim 5, wherein R$^9$ is —C$_{1-9}$alkylR$^{11}$.

7. The compound of claim 6, wherein R$^{11}$ is substituted or unsubstituted aryl or substituted or unsubstituted heteroaryl.

8. The compound of claim 7, wherein R$^{11}$ is thien-2-yl.

9. The compound of claim 1, wherein R$^1$ is —N(R$^9$)C(=O)C(=NR$^{10}$)R$^9$.

10. The compound of claim 1, wherein R$^1$ is —N(R$^9$)C(=O)C(=C R$^9$R$^{10}$)R$^9$.

11. The compound of claim 1, wherein R$^9$ is —C$_{1-9}$alkyl.

12. The compound of claim 1, wherein R$^9$ is —C$_{1-9}$alkylR$^{11}$.

13. The compound of claim 1, wherein R$^9$ is —C$_{1-9}$alkylCO$_2$R$^{12}$.

14. The compound of claim 1, wherein R$^9$ is substituted or unsubstituted heteroaryl.

15. The compound of claim 1, wherein G$^1$ is a bond.

16. The compound of claim 1, wherein G$^2$ is —C(R$^e$R$^f$)—.

17. The compound of claim 1, wherein G$^2$ is —C(=O)—.

18. The compound of claim 1, wherein G$^2$ is —C(=O)C(R$^e$R$^f$)—.

19. The compound of claim 1, wherein G$^1$ is —C(R$^a$R$^b$)— and G$^2$ is —C(R$^e$R$^f$)—.

20. The compound of claim 1, wherein Z is —O—.

21. The compound of claim 1, wherein Z is —S—.

22. The compound of claim 1, wherein Z is —N(R$^9$)—.

23. The compound of claim 1, wherein Z is —N[C(=O)R$^9$]—.

24. The compound of claim 1, wherein Z is —N[C(=O)OR$^9$]—.

25. The compound of claim 1, wherein Z is —N(R$^k$)—.

26. The compound of claim 1, wherein Y is CR$^6$.

27. The compound of claim 1, wherein Y is N.

28. The compound of claim 1, wherein m is 1.

29. The compound of claim 1, wherein R$^7$ and R$^8$ are H.

30. The compound of claim 1, wherein R$^{10}$ is —OR$^9$—.

31. The compound of claim 1, wherein R$^{10}$ is —C(=O)OR$^9$—.

32. The compound of claim 1, wherein R$^{11}$ is substituted or unsubstituted aryl.

33. The compound of claim 1, wherein R$^{11}$ is substituted or unsubstituted heteroaryl.

34. The compound of claim 1, wherein R$^{11}$ is substituted or unsubstituted carbocyclyl.

35. The compound of claim 1, wherein R$^{11}$ is substituted or unsubstituted heterocyclyl.

36. The compound of claim 1, wherein X is —CO$_2$R$^{12}$ or carboxylic acid isosteres.

37. The compound of claim 36, wherein X is —CO$_2$H.

38. The compound of claim 1, having a structure selected from the group consisting of:

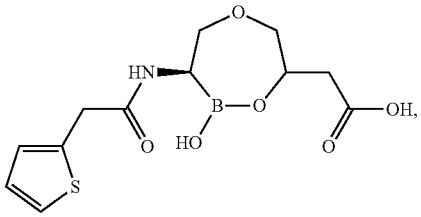

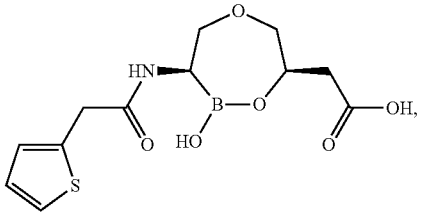

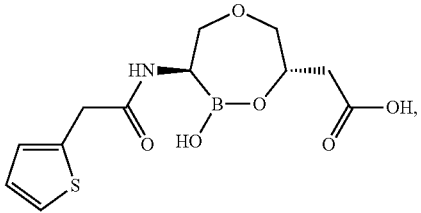

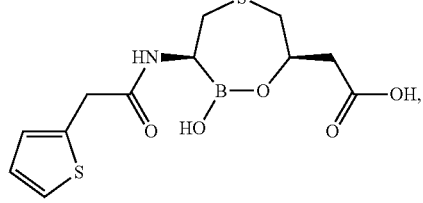
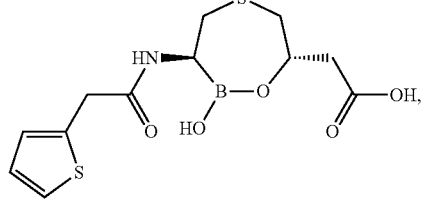
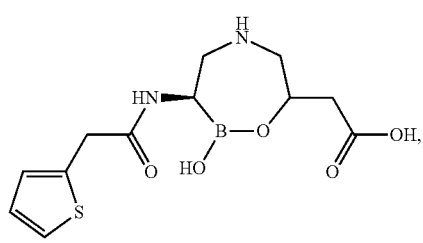
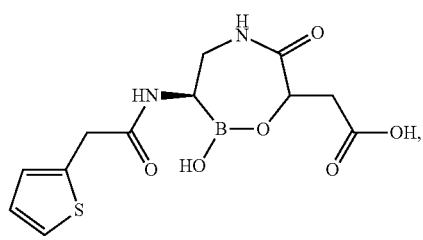
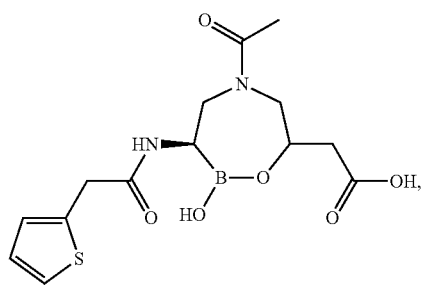
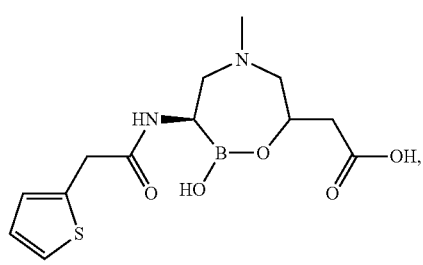
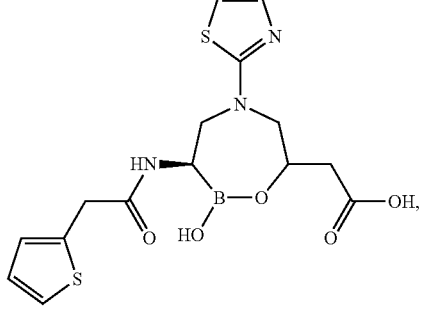
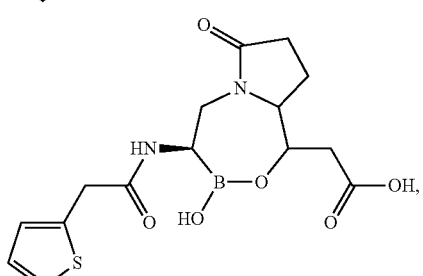
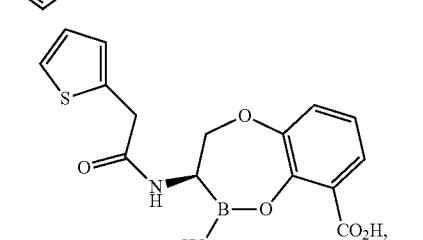
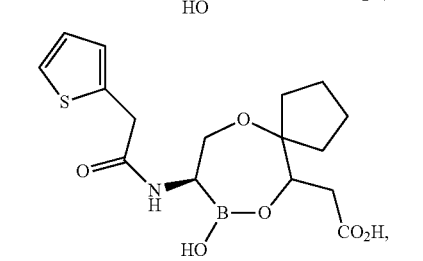
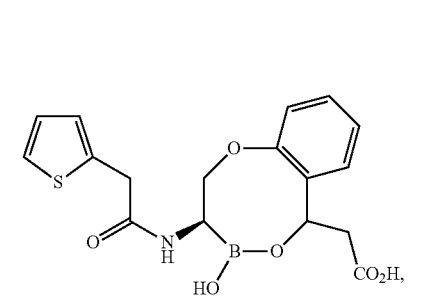
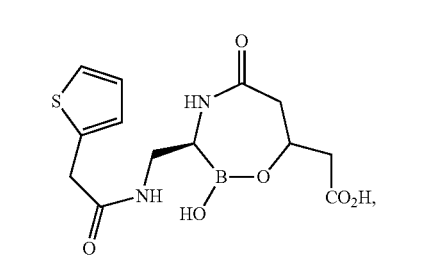

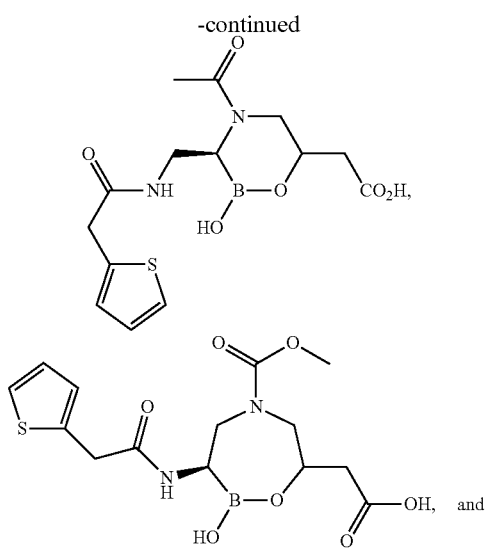
39. A pharmaceutical composition comprising a therapeutically effective amount of a compound according to claim 1 or a pharmaceutically acceptable salt thereof and a pharmaceutically acceptable excipient.
* * * * *

UNITED STATES PATENT AND TRADEMARK OFFICE
CERTIFICATE OF CORRECTION

PATENT NO. : 9,012,491 B2  
APPLICATION NO. : 14/241412  
DATED : April 21, 2015  
INVENTOR(S) : Reddy et al.

It is certified that error appears in the above-identified patent and that said Letters Patent is hereby corrected as shown below:

Title Page

In column 1 (page 2, item 56) at line 73, Under Other Publications, change "treament"," to --treatment",--.

In column 2 (page 2, item 56) at line 28, Under Other Publications, change "AICI3" to --AlCl3--.

In column 1 (page 3, item 56) at line 18, Under Other Publications, change "persistance"," to --persistence",--.

In column 1 (page 3, item 56) at line 29, Under Other Publications, change "Acitve" to --Active--.

In column 2 (page 3, item 56) at line 69, Under Other Publications, change ""Assymmetric" to --"Asymmetric--.

In column 2 (page 4, item 56) at line 5, Under Other Publications, change "Tetrahed" to --Tetrahedron--.

In the Specification

In column 1 at line 36, Change "costs" to --costs.--.

In column 5 at line 62, Change "Pheneticillin," to --Phenethicillin,--.

In column 6 at line 4, Change "Cefinetazole," to --Cefmetazole,--.

In column 6 at line 6, Change "Cefinenoxime," to --Cefmenoxime,--.

In column 12 at line 17, change "pyrridyl," to --pyridyl,--.

In column 20 at line 23, Change "intrapulmonarilly," to --intrapulmonary,--.

In column 21 at line 30, Change "hydrotropies," to --hydrotropes,--.

In column 21 at lines 66-67, Change "croscarmelose;" to --croscarmellose;--.

In column 24 at line 53, Change "Pheneticillin," to --Phenethicillin,--.

In column 24 at line 62, Change "Cefinetazole," to --Cefmetazole,--.

In column 24 at line 64, Change "Cefinenoxime," to --Cefmenoxime,--.

Signed and Sealed this  
First Day of March, 2016

Michelle K. Lee  
*Director of the United States Patent and Trademark Office*

In column 25 at line 50, Change "Nisseria," to --Neisseria,--.
In column 25 at line 50, Change "Baccillus," to --Bacillus,--.
In column 45 at line 7, Change "though" to --through--.
In column 45 at line 19, Change "silanyloxy)-" to --silyloxy)- --.
In column 45 at line 36, Change "56 pt," to --56 µL,--.
In column 46 at line 59, Change "125 pt," to --125 µL--.
In column 46 at line 61, Change "39 pt," to --39 µL,--.
In the Claims
In column 67 at lines 11-20 (approx.), claim 2, Change
"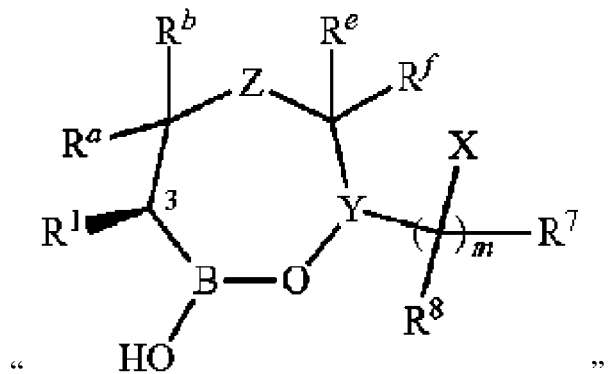"
to
-- 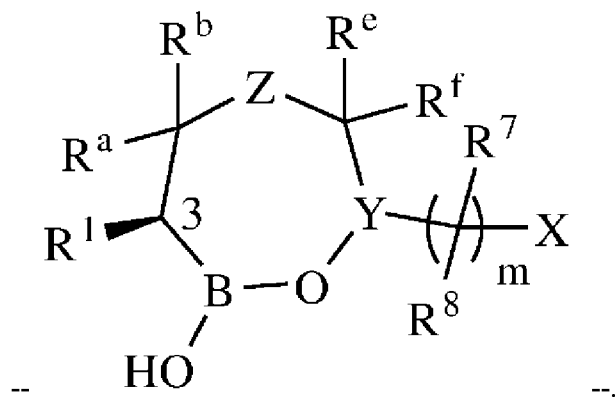 --.

CERTIFICATE OF CORRECTION (continued)

U.S. Pat. No. 9,012,491 B2

In column 67 at lines 25-35 (approx.), claim 3, Change

"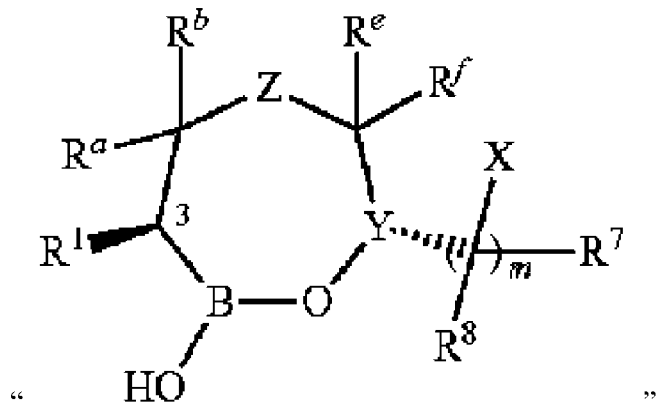"

to

--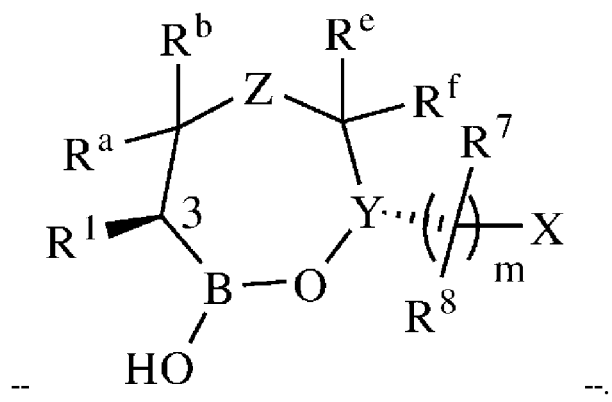--.

In column 67 at lines 40-49 (approx.), claim 4, Change

"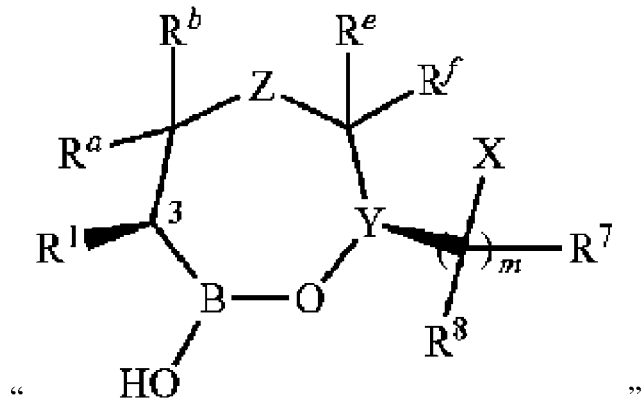"

to
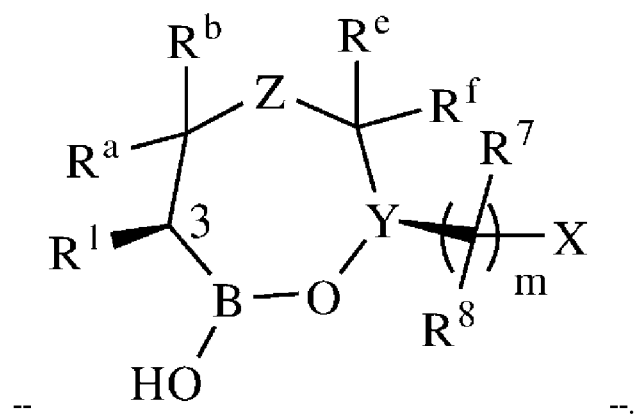
--.